(12) United States Patent
Cutrer et al.

(10) Patent No.: US 8,226,539 B2
(45) Date of Patent: Jul. 24, 2012

(54) BRACHYTHERAPY APPARATUS FOR ASYMMETRICAL BODY CAVITIES

(75) Inventors: L. Michael Cutrer, Huntington Beach, CA (US); Richard A. Terwilliger, Grants Pass, OR (US); Fredrick W. Winch, Snohomish, WA (US); John Zhang, Lake Forest Park, WA (US); Wayne Higgins, Malden, MA (US); Terence Ellard, Seattle, WA (US); David Bossi, Simi Valley, CA (US)

(73) Assignee: Portola Medical, Inc., Portola Valley, CA (US)

( * ) Notice: Subject to any disclaimer, the term of this patent is extended or adjusted under 35 U.S.C. 154(b) by 238 days.

(21) Appl. No.: 12/554,732

(22) Filed: Sep. 4, 2009

(65) Prior Publication Data

US 2009/0326314 A1 Dec. 31, 2009

Related U.S. Application Data

(63) Continuation of application No. 11/379,739, filed on Apr. 21, 2006, now abandoned, which is a continuation-in-part of application No. 11/305,437, filed on Dec. 16, 2005, now Pat. No. 8,137,256.

(51) Int. Cl.
*A61N 5/00* (2006.01)
(52) U.S. Cl. ............................................................ 600/3
(58) Field of Classification Search .................... 600/1–8
See application file for complete search history.

(56) References Cited

U.S. PATENT DOCUMENTS

| 3,224,432 A | 12/1965 | Billingsley |
| 3,807,386 A | 4/1974 | Rocoplan et al. |
| 3,872,856 A | 3/1975 | Clayton |
| 3,927,325 A | 12/1975 | Hungate et al. |
| 4,434,789 A | 3/1984 | Kumar |

(Continued)

FOREIGN PATENT DOCUMENTS

CA 2296430 B1 6/2004

(Continued)

OTHER PUBLICATIONS

Anbai, A. et al. 1998. Brachytherapy with Iridium-192 Thin Wire for Head and Neck Carcinoma. Jibi Inkoka, Tokeibu Geka (Otolaryngology—Head and Neck Surgery), 1998, vol. 70, No. 7, pp. 417-421. (Abstract only).

(Continued)

*Primary Examiner* — Samuel Gilbert
(74) *Attorney, Agent, or Firm* — Locke Lord LLP

(57) ABSTRACT

The present disclosure provides a brachytherapy apparatus, system and method that delivers partial breast irradiation treatment for post-lumpectomy patients via introduction of a catheter-like device through a trocar. The apparatus may be introduced post-surgically with local anesthesia under image guidance into the previous excision site and into a cavity by a surgeon. The brachytherapy apparatus includes one or more thin-walled tubes, each of said thin-walled tubes being configured to contain one or more radioactive sources, at least one radiation source configured to deliver a prescribed dose of radiation, a whisk adjuster configured to permit adjustment of each of the one or more thin-walled tubes so that the tubes substantially conform to a size of the body cavity; and an expansion element configured to expand outwardly said one or more thin-walled tubes within the cavity so that the thin-walled tubes substantially conform to a shape and/or size of the body cavity.

5 Claims, 37 Drawing Sheets

U.S. PATENT DOCUMENTS

| | | |
|---|---|---|
| 4,584,991 A | 4/1986 | Tokita et al. |
| 4,763,642 A | 8/1988 | Horowitz |
| 4,815,449 A | 3/1989 | Horowitz |
| 4,976,680 A | 12/1990 | Hayman et al. |
| 5,007,437 A | 4/1991 | Sterzer |
| 5,050,930 A | 9/1991 | Schuster et al. |
| 5,092,834 A * | 3/1992 | Bradshaw et al. ............... 600/7 |
| 5,120,973 A * | 6/1992 | Rohe et al. ............... 250/497.1 |
| 5,125,925 A | 6/1992 | Lundahl |
| 5,147,282 A | 9/1992 | Kan |
| 5,317,616 A | 5/1994 | Swerdloff et al. |
| 5,336,178 A | 8/1994 | Kaplan et al. |
| 5,345,936 A | 9/1994 | Pomeranz et al. |
| 5,411,466 A | 5/1995 | Hess |
| 5,429,582 A | 7/1995 | Williams |
| 5,431,648 A | 7/1995 | Lev |
| 5,484,384 A | 1/1996 | Fearnot |
| 5,540,659 A | 7/1996 | Teirstein |
| 5,611,767 A | 3/1997 | Williams |
| 5,623,940 A | 4/1997 | Daikuzono |
| 5,643,171 A | 7/1997 | Bradshaw et al. |
| 5,653,683 A | 8/1997 | D'Andrea |
| 5,662,580 A | 9/1997 | Bradshaw et al. |
| 5,678,572 A | 10/1997 | Shaw et al. |
| 5,683,345 A | 11/1997 | Waksman et al. |
| 5,688,220 A | 11/1997 | Verin et al. |
| 5,720,717 A * | 2/1998 | D'Andrea ............... 604/21 |
| 5,730,698 A | 3/1998 | Fischell et al. |
| 5,817,104 A | 10/1998 | Bilitz et al. |
| 5,836,868 A | 11/1998 | Ressemann et al. |
| 5,840,008 A | 11/1998 | Klein et al. |
| 5,851,171 A | 12/1998 | Gasson |
| 5,855,546 A | 1/1999 | Hastings et al. |
| 5,863,284 A | 1/1999 | Klein |
| 5,863,285 A | 1/1999 | Coletti |
| 5,879,282 A | 3/1999 | Fischell et al. |
| 5,904,680 A | 5/1999 | Kordis et al. |
| 5,910,101 A | 6/1999 | Andrews et al. |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,968,040 A | 10/1999 | Swanson et al. |
| 6,011,995 A | 1/2000 | Guglielmi et al. |
| 6,022,308 A | 2/2000 | Williams |
| 6,030,333 A | 2/2000 | Sioshansi et al. |
| 6,036,631 A | 3/2000 | McGrath et al. |
| 6,050,930 A | 4/2000 | Teirstein |
| 6,059,812 A | 5/2000 | Clerc et al. |
| 6,066,083 A | 5/2000 | Slater et al. |
| 6,074,339 A | 6/2000 | Gambale et al. |
| 6,083,148 A | 7/2000 | Williams |
| 6,149,574 A | 11/2000 | Trauthen et al. |
| 6,152,869 A | 11/2000 | Park et al. |
| 6,196,963 B1 | 3/2001 | Williams |
| 6,196,996 B1 | 3/2001 | Teirstein |
| 6,200,257 B1 | 3/2001 | Winkler |
| 6,213,976 B1 | 4/2001 | Trerotola |
| 6,216,043 B1 | 4/2001 | Swanson et al. |
| 6,217,503 B1 | 4/2001 | Weinberger et al. |
| 6,238,374 B1 | 5/2001 | Winkler |
| 6,263,236 B1 | 7/2001 | Kasinkas et al. |
| 6,267,775 B1 | 7/2001 | Clerc et al. |
| 6,338,709 B1 | 1/2002 | Geoffrion et al. |
| 6,391,026 B1 | 5/2002 | Hung et al. |
| 6,409,652 B1 | 6/2002 | Kamdar et al. |
| 6,413,203 B1 | 7/2002 | Sahatjian |
| 6,413,204 B1 | 7/2002 | Winkler et al. |
| 6,482,142 B1 | 11/2002 | Winkler et al. |
| 6,537,194 B1 | 3/2003 | Winkler |
| 6,554,760 B2 | 4/2003 | Lamoureux et al. |
| 6,589,158 B2 | 7/2003 | Winkler |
| 6,607,476 B1 | 8/2003 | Barnhart |
| 6,607,477 B1 | 8/2003 | Longton et al. |
| 6,607,478 B2 | 8/2003 | Williams |
| 6,638,727 B1 | 10/2003 | Hung et al. |
| 6,642,010 B2 | 11/2003 | Love et al. |
| 6,652,548 B2 | 11/2003 | Evans et al. |
| 6,659,105 B2 | 12/2003 | Burbank et al. |
| 6,673,006 B2 | 1/2004 | Winkler |
| 6,676,658 B2 | 1/2004 | Burbank et al. |
| 6,685,718 B1 | 2/2004 | Wyzgala et al. |
| 6,695,760 B1 | 2/2004 | Winkler et al. |
| 6,712,816 B2 | 3/2004 | Hung et al. |
| 6,743,184 B2 | 6/2004 | Sampson et al. |
| 6,749,555 B1 | 6/2004 | Winkler et al. |
| 6,770,058 B1 | 8/2004 | Liprie |
| 6,840,936 B2 | 1/2005 | Sliwa et al. |
| 6,855,160 B1 | 2/2005 | Gambale et al. |
| 6,872,183 B2 | 3/2005 | Sampson et al. |
| 6,893,450 B2 | 5/2005 | Foster |
| 6,923,754 B2 | 8/2005 | Lubock |
| 6,955,641 B2 | 10/2005 | Lubock |
| 6,976,949 B2 | 12/2005 | Winkler et al. |
| 6,994,688 B2 | 2/2006 | Brauckman et al. |
| 7,063,670 B2 | 6/2006 | Sampson et al. |
| 2001/0021826 A1 | 9/2001 | Winkler |
| 2002/0133151 A1 | 9/2002 | Hung et al. |
| 2002/0173816 A1 | 11/2002 | Hung |
| 2002/0193653 A1 | 12/2002 | Winkler |
| 2003/0022161 A1 | 1/2003 | Love et al. |
| 2003/0032851 A1 | 2/2003 | Apple et al. |
| 2003/0039959 A1 | 2/2003 | Love et al. |
| 2003/0049262 A1 | 3/2003 | Love et al. |
| 2003/0092957 A1 | 5/2003 | Scott et al. |
| 2003/0149329 A1 | 8/2003 | O'Foghludha |
| 2003/0191412 A1 | 10/2003 | Sampson et al. |
| 2004/0016728 A1 | 1/2004 | Liu et al. |
| 2004/0023912 A1 | 2/2004 | Hung |
| 2004/0029202 A1 | 2/2004 | Love et al. |
| 2004/0054368 A1 | 3/2004 | Truckai et al. |
| 2004/0091423 A1 | 5/2004 | Hung et al. |
| 2004/0109823 A1 | 6/2004 | Kaplan |
| 2004/0116767 A1 | 6/2004 | Lebovic et al. |
| 2004/0167372 A1 | 8/2004 | Winkler et al. |
| 2004/0191854 A1 | 9/2004 | Lapen et al. |
| 2004/0210101 A1 | 10/2004 | Winkler |
| 2004/0215099 A1 | 10/2004 | Sampson et al. |
| 2004/0224347 A1 | 11/2004 | Love et al. |
| 2005/0004471 A1 | 1/2005 | Hogendijk et al. |
| 2005/0027157 A1 | 2/2005 | Winkler et al. |
| 2005/0085681 A1 | 4/2005 | Stubbs et al. |
| 2005/0101823 A1 | 5/2005 | Linares et al. |
| 2005/0101824 A1 | 5/2005 | Stubbs |
| 2005/0101825 A1 | 5/2005 | Winkler et al. |
| 2005/0101860 A1 | 5/2005 | Patrick et al. |
| 2005/0107653 A1 | 5/2005 | Patrick et al. |
| 2005/0113629 A1 | 5/2005 | Patrick et al. |
| 2005/0124843 A1 | 6/2005 | Singh |
| 2005/0131267 A1 | 6/2005 | Talmadge |
| 2005/0131268 A1 | 6/2005 | Talmadge |
| 2005/0131269 A1 | 6/2005 | Talmadge |
| 2005/0137498 A1 | 6/2005 | Sakal et al. |
| 2005/0137499 A1 | 6/2005 | Sheets et al. |
| 2005/0149159 A1 | 7/2005 | Andreas |
| 2005/0182286 A1 | 8/2005 | Lubock |
| 2005/0240073 A1 | 10/2005 | Apffelstaedt et al. |
| 2006/0014997 A1 | 1/2006 | Kindlein et al. |
| 2006/0020156 A1 | 1/2006 | Shukla |
| 2006/0047178 A1 | 3/2006 | Winkler et al. |
| 2006/0063961 A1 | 3/2006 | Drobnik et al. |
| 2006/0094923 A1 | 5/2006 | Mate |
| 2006/0100475 A1 | 5/2006 | White et al. |
| 2006/0116546 A1 | 6/2006 | Eng |
| 2006/0129128 A1 | 6/2006 | Sampson |
| 2006/0135956 A1 | 6/2006 | Sampson et al. |
| 2007/0049786 A1 | 3/2007 | Edmundson |
| 2007/0106108 A1 | 5/2007 | Hermann et al. |
| 2007/0142695 A1 | 6/2007 | White et al. |

FOREIGN PATENT DOCUMENTS

| | | |
|---|---|---|
| CA | 2394562 B1 | 11/2004 |
| EP | 0810004 A2 | 12/1997 |
| EP | 8676200 | 9/1998 |
| EP | 0770258 B1 | 10/2001 |
| EP | 0955071 B1 | 2/2004 |
| EP | 1426063 A2 | 6/2004 |

| | | | |
|---|---|---|---|
| EP | 1568397 A1 | 8/2005 |
| EP | 1239920 B1 | 5/2006 |
| EP | 0998330 B1 | 5/2009 |
| JP | 03-30760 | 2/1991 |
| JP | 2006-26443 A1 | 2/2006 |
| RU | 2089143 C1 | 9/1997 |
| RU | 2128060 C1 | 3/1999 |
| WO | 96-02059 A1 | 1/1996 |
| WO | 9815315 A1 | 4/1998 |
| WO | 9902219 A1 | 1/1999 |
| WO | 9904856 A1 | 2/1999 |
| WO | 9922812 A1 | 5/1999 |
| WO | 9924117 A1 | 5/1999 |
| WO | 9933515 A2 | 7/1999 |
| WO | 0143826 A1 | 6/2001 |
| WO | 2007056714 A1 | 5/2007 |

OTHER PUBLICATIONS

Armstrong, J.G. et al. The Use of a Prosthetic Tissue Expander to Displace Bowel from a Brachytherapy Implant Site. International Journal of Radiation Oncology, Biology, Physics, Dec. 1990, vol. 19, No. 6, pp. 1521-1523.

Balter, S. 1998. Endovascular Brachytherapy: Physics and Technology. Catheterization and Cardiovascular Diagnosis, 1998, vol. 45, No. 3, pp. 292-298.

Benitez, P.R. et al. 2006. Preliminary Results and Evaluation of MammoSite Balloon Brachytherapy for Partial Breast Irradiation for Pure Ductal Carcinoma In Situ: A Phase II Clinical Study. American Journal of Surgery, 2006, vol. 192, No. 4, pp. 427-433.

Diederich, C.J. et al. 1996. Direct-Coupled Interstitial Ultrasound Applicators for Simultaneous Thermobrachytherapy: A Feasibility Study. International Journal of Hyperthermia, May-Jun. 1996, vol. 12, No. 3, pp. 401-419.

Do, L. et al. 2006. LDR Brachytherapy Implants as a Boost in Early Stage Breast Cancer in Women with Cilastic Implants. In Proceedings of the American Brachytherapy Society, 27th Annual Meeting, 2006, vol. 5, No. 2, p. 95. (Abstract only).

Fukui, A. et al. 1999. Problems of Treatment Planning of Intracavitary Brachytherapy for Advanced Esophageal Cancer. Rinsho Hoshasen (Japanese Journal of Clinical Radiology), 1999, vol. 44, No. 8, pp. 981-984. (In Japanese, Abstract only).

Gildenberg, P.L. et al. 1994. Fractionated Brachytherapy: Catheter Insertion and Dosimetry. Stereotact. Funct. Neurosurg. 1994, vol. 63, Nos. 1-4, pp. 246-249.

Hirschberg, H. et al. 1999. An Indwelling Brachytherapy Balloon Catheter: Potential Use as an Intracranial Light Applicator for Photodynamic Therapy. Journal of Neuro-Oncology, Aug. 1999, vol. 44, No. 1, pp. 15-21.

Inakoshi H. et al. 1993. A New Radiotherapy Planning Program Using a New Double-Lumen Balloon Applicator for High-Dose-Rate Intracavity Irradiation of Esophageal Cancer. Rinsho Hoshasen (Japanes Journal of Clinical Radiology), 1993, vol. 38, No. 5, pp. 565-569. (In Japanese, Abstract only).

International Search Report and Written Opinion of the International Searching Authority, mailed Apr. 4, 2008, for PCT Application No. PCT/US06/45081 (international application corresponding to parent U.S. Appl. No. 11/379,739).

Jani, S.K. et al. 1989. Dose Anisotropy Around an Au-198 Seed Source. Medical Physics, Jul.-Aug. 1989, vol. 16, No. 4, pp. 632-635.

Kubo, H.D. et al. 1999. Impact of Collimator Leaf Width on Stereotactic Radioosurgery and 3D Conformal Radiotherapy Treatment Plans. International Journal of Radiation Oncology Biology Physics, Jul. 1, 1999, vol. 44, No. 4, pp. 937-945.

Kuske, R.R. et al. 2000. Wide Volume Brachytherapy Alone for Select Breast Cancers: The Ten Year Experience of the Ochsner Clinic. International Journal of Radiation Oncology Biology Physics, 2000: vol. 48, No. 3; Suppl. 1, p. 2063. (Abstract only).

Malgieri, M. 1996. Relative Effects of Different Modalities of Brachytherapy on Late Responding Tissues and Tumours. Radiotherapy and Oncology, 1996, vol. 39, No. Sup. 1, p. 88. (Abstract only).

Marinello, G. et al. 1985. Comparative Dosimetry Between Iridium Wires and Seed Ribbons. International Journal of Radiation Oncology, Biology, Physics, Sep. 1985, vol. 11, No. 9, pp. 1733-1739.

Mazeron, J.J. et al. 1985. Treatment of Bladder Tumors by Iridium 192 Implantation. The Creteil Technique. Oncology (Netherlands), 1985, vol. 4, No. 2, pp. 111-119.

Muller-Runkel R. et al. 1987. Brachytherapy Implants with Differently Spaced Ir-192 Seeds: A Dosimetric Study. Radiology, Oct. 1987, vol. 165, No. 1, pp. 271-274.

Ogawa, K. et al. 1999. Intraluminal Brachytherapy Using a Balloon Applicator for Superficial Esophageal Carcinoma: Importance of Applicator Confirmation by Computed Tomography. Radiation Medicine, 1999, vol. 17, No. 5, pp. 399-401.

Pierquin, B. et al. 1988. Intracavitary Irradiation of Carcinomas of the Uterus and Cervix: The Cretail Method. International Journal of Radiation Oncology, Biology, Physics, Dec. 1988, vol. 15, No. 6, pp. 1465-1473.

Popowski, Y. et al. 1995. Intra-arterial 90Y Brachytherapy: Preliminary Dosimetric Study Using a Specially Modified Angioplasty Balloon. International Journal of Radiation Oncology Biology Physics, Oct. 1995, vol. 33, No. 3, pp. 713-717.

Rownd, J. 2005. Applicator Design and Dose Distributions. In Medical Physics Monograph, No. 31, pp. 797-804 (Madison, WI: Medical Physics Publishing, 2005).

Sealy, R. et al. 1984. The Treatment of Cancer of the Uvula and Soft Palate with Interstitial Radioactive Wire Implants. International Journal of Radiation Oncology, Biology, Physics, 1984, vol. 10, No. 10, pp. 1951-1955.

U.S. Appl. No. 60/625,355, entitled "Expandable Brachytherapy Device," filed Nov. 5, 2004.

U.S. Appl. No. 60/735,649, entitled "Brachytherapy Apparatus and Methods of Using Same," filed Nov. 10, 2005.

Xu, Z. et al. 1997. The Investigation of 32P Wire for Catheter-Based Endovascular Irradiation. Medical Physics, Nov. 1997, vol. 24, No. 11, pp. 1788-1792.

Yorozu, A. et al. 1999. Curative Radiotherapy with High-Dose-Rate Brachytherapy Boost for Localized Esophageal Carcinoma: Dose-Effect Relationship of Brachytherapy with the Balloon Type Applicator System. Radiotherapy and Oncology, May 1999, vol. 51, No. 2, pp. 133-139.

Zavgorodni, S.F. et al. 1999. Comparison of Three Simply Radiosurgery Techniques for Treating Elongated Lesions. Physica Medica, Apr.-Jun. 1999, vol. 15, No. 2, pp. 57-62.

* cited by examiner

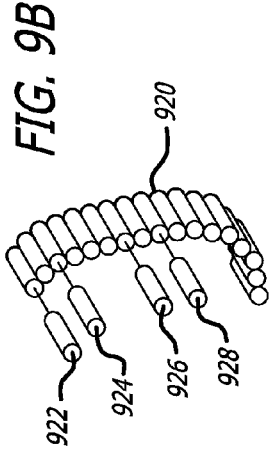
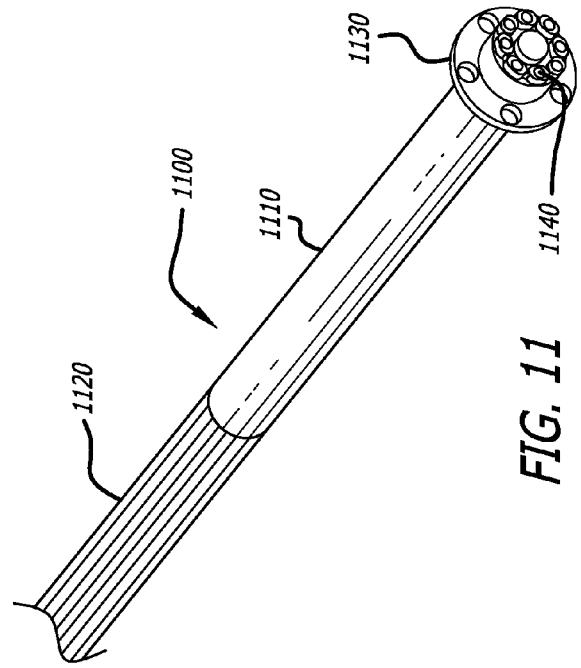
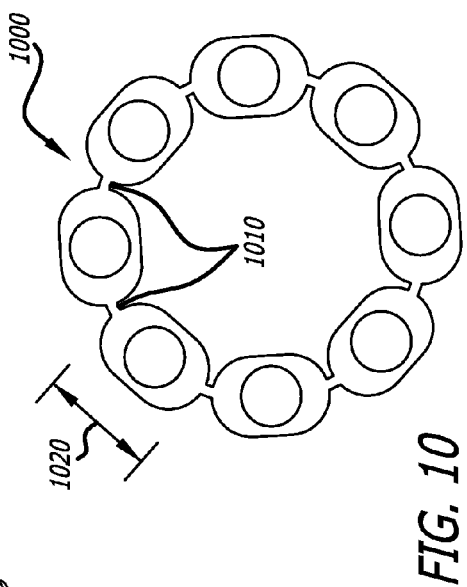
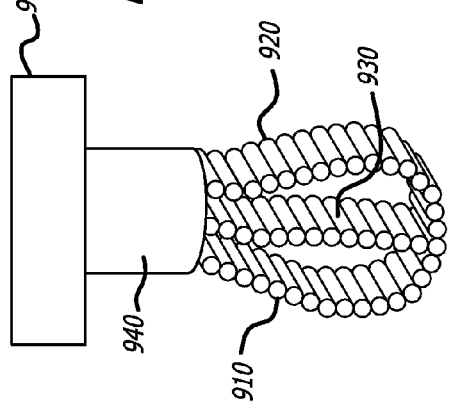
FIG. 9A
FIG. 9B
FIG. 10
FIG. 11

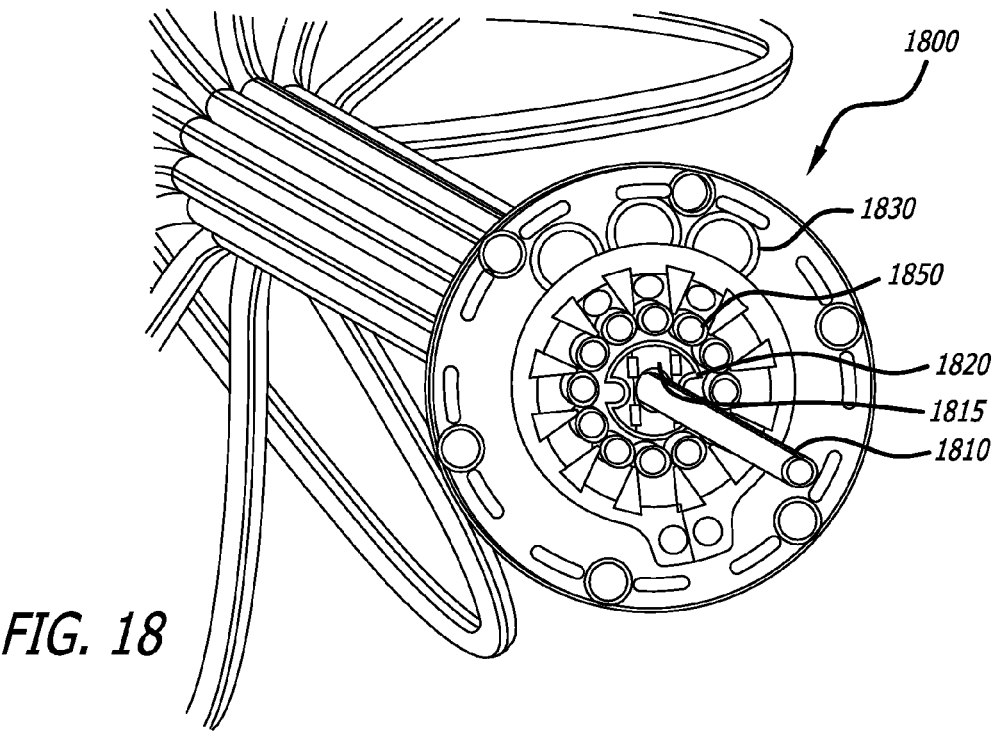
FIG. 18
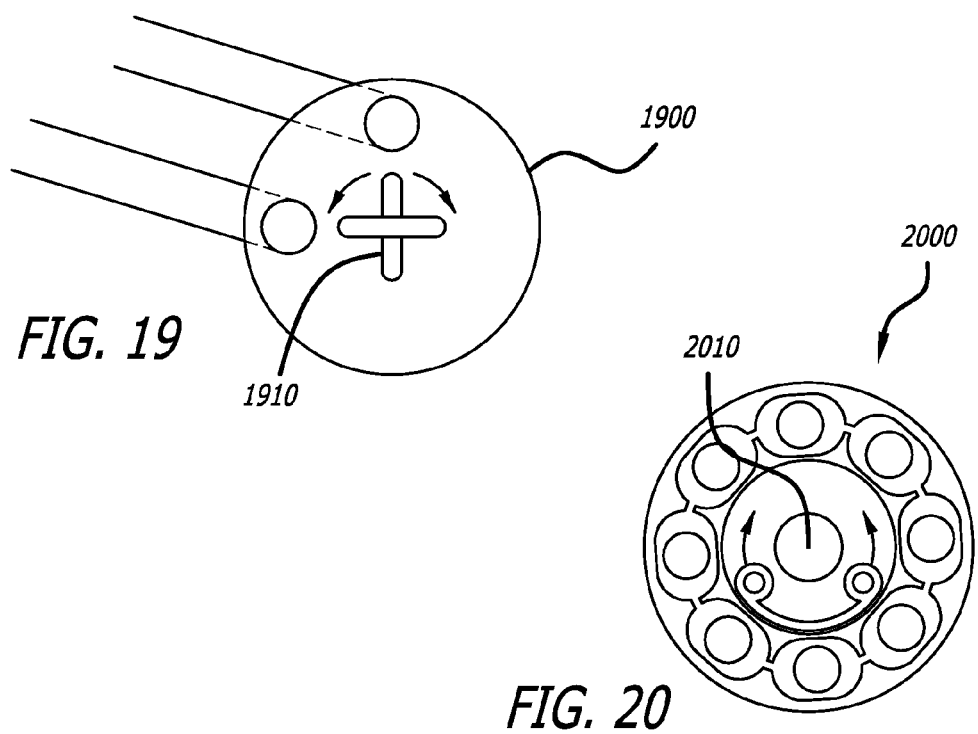
FIG. 19
FIG. 20

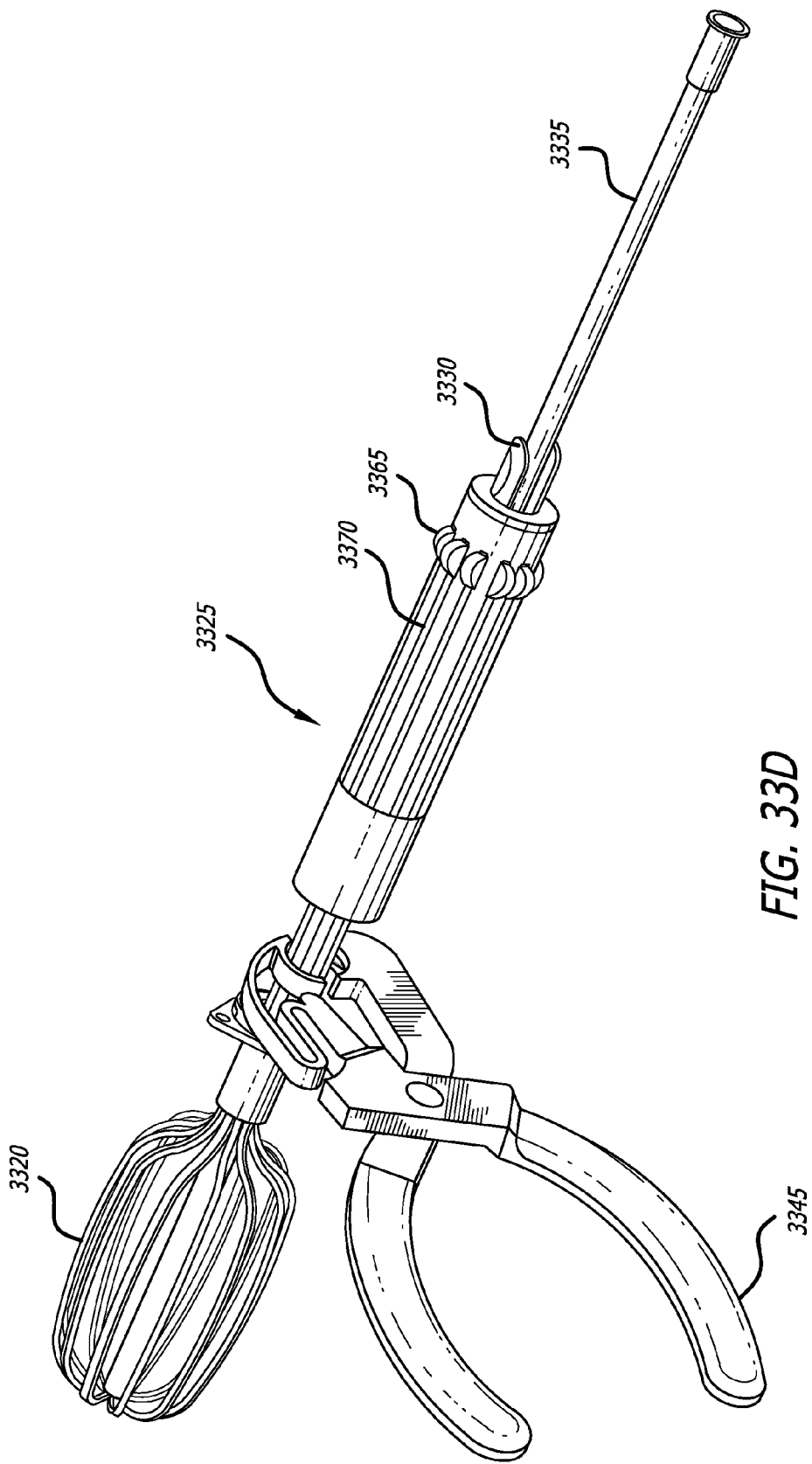

BRACHYTHERAPY APPARATUS FOR ASYMMETRICAL BODY CAVITIES

CROSS REFERENCE TO RELATED APPLICATIONS

This application is a continuation of U.S. patent application Ser. No. 11/379,739, filed Apr. 21, 2006, entitled "Brachytherapy Apparatus for Asymmetrical Body Cavities," which is a continuation-in-part of U.S. patent application Ser. No. 11/305,437, filed Dec. 16, 2005, entitled "Brachytherapy Apparatus." The content of both applications is incorporated herein by reference.

BACKGROUND

1. Field

The present disclosure relates to radiation treatment and more particularly, to an apparatus and method that allows cancer patients to receive a low dose radiation treatment after removal of a tumor.

2. Description of Related Art

Today, a number of treatment options exist for patients who are diagnosed with cancer. With respect to breast cancer, mastectomies commonly have been used. A mastectomy involves removal of all or a part of the breast tissue, and sometimes also involves removal of the underlying pectoral muscles and lymph nodes around the breasts. Mastectomies may be accompanied by significant scarring, thus adversely affecting the aesthetic appearance or cosmesis of the breast and surrounding tissue. Moreover, removal of all or large regions of the breast may have an associated significant physical trauma as well as psychological trauma.

Various alternative treatment options have been developed to address adverse affects associated with mastectomies. These alternative treatment options may involve a breast-sparing lumpectomy. A lumpectomy tends to involve removal of only the portion or "lump" of the breast that contains tissue having tumors. The remaining tissue outside the removed lump may be treated subsequently with breast irradiation that is designed to treat abnormal or suspect tissue that surrounds the removed tumor.

One of the various lumpectomy options involves full breast irradiation. While this option incorporates the breast-sparing lumpectomy, the treatment time may last for several weeks, with several treatments a day during those weeks. At times, the number of treatments may be as much as thirty treatments. Such a high number of treatments may be not only inconvenient for the patient, it may also be expensive since each time the patient sees a doctor, a charge may follow. Even for insured patients, all of the charges may not be covered by the patient's insurance.

Moreover, lumpectomies involving full breast irradiation may result in significant surface tissue damage of healthy tissue since the entire breast is being irradiated. Likewise, the cosmesis or aesthetic appearance of the breast may be compromised since the entire breast is being irradiated. Moreover, because more tissue is affected, the risk of complications may increase with full breast irradiation.

In order to address the consequences of full breast irradiation procedures, partial breast irradiation procedures have been developed. These options may incorporate high dose radiation. With high-dose irradiation, significant patient discomfort may result since multiple needles and catheters are placed into the breast. Moreover, there is a greater chance that surface tissue damage may occur, resulting in scarring and sensitivity due to the use of the multiple needles and catheters.

Another example of a treatment option that has been developed incorporating partial breast irradiation is one developed by Proxima Therapeutics, Inc., and known as the MAMMOSITE™ radiation therapy treatment system. This system appears to be designed to address some of the drawbacks associated with full breast irradiation while also addressing some of the drawbacks associated with high-dose radiation. The procedure involves inflating a balloon so that it fills the empty cavity and inserting a high-dose radiation source for delivery inside the cavity. The treatment time may be twice a day for five (5) days, for a total of ten (10) treatments. However, the patient selection criteria may be limited in that patients with small breasts may not be good candidates. For example, the breast may be too small to allow proper inflation of the balloon since the balloon relies on air for expansion.

Recently, brachytherapy has been used for partial breast irradiation to deliver a more localized treatment of tumor cells after a lumpectomy. Partial breast irradiation is used to supplement surgical resection by targeting the residual tumor margin after resection, with the goal of treating any residual cancer in the margin. Radiation therapy can be administered through one of several methods, or a combination of methods, including external-beam radiation, stereotactic radiosurgery, and permanent or temporary interstitial brachytherapy. Owing to the proximity of the radiation source, brachytherapy offers the advantage of delivering a more localized dose to the target tissue region.

There is a need for an instrument and associated procedure which can be used to deliver radiation from a radioactive source to target tissue with a desired intensity and without over-exposure of body tissues disposed between the radiation source and the target.

There is further a need for an instrument and associated procedure that has broad patient selection criteria with reduced office visits.

There is yet further a need for an irradiation procedure that is appropriate not only for breasts, but may be used in treatment regimens for other areas of the body, such as the brain and prostate.

BRIEF SUMMARY

The present disclosure addresses the deficiencies noted hereinabove by providing an interstitial brachytherapy apparatus that may be implanted in a single visit, thereby reducing the number of office visits and providing a more convenient treatment regimen.

In accordance with one embodiment of the present disclosure, a brachytherapy apparatus is provided for delivery of localized irradiation after surgical tissue removal, where the tissue removal results in a body cavity surrounded by remaining tissue. The apparatus comprises one or more thin-walled tubes, each of said thin-walled tubes being configured to contain one or more radioactive sources. The apparatus further comprises at least one radiation source configured to deliver a prescribed dose of radiation, and a whisk adjuster configured to permit adjustment of each of the one or more thin-walled tubes so that the tubes substantially conform to a size of the body cavity. Moreover, the apparatus comprises an expansion element configured to expand outwardly said one or more thin-walled tubes within the cavity so that the thin-walled tubes substantially conform to a shape and/or size of the body cavity.

In accordance with another embodiment of the present disclosure, a brachytherapy apparatus is provided for delivery of localized irradiation after surgical tissue removal, the tissue removal resulting in a body cavity surrounded by remaining tissue. The apparatus comprises one or more thin-walled tubes, each of said thin-walled tubes being configured to contain one or more radioactive sources, and at least one radiation source configured to deliver a prescribed dose of radiation. The apparatus further comprises a whisk adjuster configured to permit adjustment of each of the one or more thin-walled tubes so that the tubes substantially conform to a size of the body cavity, and an expansion element configured to be engaged to expand outwardly said one or more thin-walled tubes within the cavity so that the thin-walled tubes substantially conform to a shape and/or size of the body cavity. The apparatus further comprises a center core. After the expansion element is engaged, the thin-walled tubes are arranged in two substantially concentric circles around the center core. The apparatus further comprises an opening corresponding to each thin-walled tube, the opening being configured to permit insertion of the at least one radiation source into each of the one or more thin-walled tubes during or after surgical implantation of the plurality of thin-walled tubes.

In accordance with still another embodiment of the present disclosure, a brachytherapy system is provided for delivery of localized irradiation after surgical tissue removal, the tissue removal resulting in a body cavity surrounded by remaining tissue. The brachytherapy system comprises one or more thin-walled tubes, each of said thin-walled tubes being configured to contain one or more radioactive sources, and at least one radiation source configured to deliver a prescribed dose of radiation. The system further comprises a whisk adjuster configured to permit adjustment of each of the one or more thin-walled tubes so that the tubes substantially conform to a size of the body cavity, an expansion element configured to be engaged to expand outwardly said one or more thin-walled tubes within the cavity so that the thin-walled tubes substantially conform to a shape and/or size of the body cavity. The system further comprises at least one whisk clip configured to secure the thin-walled tubes and center core in place to resist a shape and/or size change of thin-walled tubes when expanded, wherein the at least one whisk clip includes a locking mechanism.

In yet a further embodiment of the present disclosure, a method is provided for delivering localized irradiation after surgical tissue removal, the tissue removal resulting in a body cavity. The method comprises creating access to the cavity. The method further comprises providing an interstitial brachytherapy apparatus which includes one or more thin-walled tubes, each of said thin-walled tubes being configured to contain one or more radiation sources. The apparatus used in the method further includes at least one radiation source configured to deliver a prescribed dose of radiation, a whisk adjuster configured to permit adjustment of each of the one or more thin-walled tubes so that the tubes substantially conform to a size of the body cavity; and an expansion element configured to expand outwardly said one or more thin-walled tubes within the cavity so that the thin-walled tubes substantially conform to the shape and/or size of the body cavity. Using this apparatus to perform the method, the method further includes placing the interstitial brachytherapy apparatus into the cavity, expanding outwardly the interstitial brachytherapy apparatus so that it substantially conforms to the shape and/or size of the cavity, inserting the at least one radiation source into the outwardly expanded thin-walled tubes, clamping the interstitial brachytherapy apparatus onto the patient, leaving the interstitial brachytherapy apparatus inside the cavity for a sufficient time to deliver the prescribed radiation dose to remaining tissue that surrounds the cavity; and removing the interstitial brachytherapy apparatus.

In still yet a further embodiment of the present disclosure, another method is provided for delivering localized irradiation after surgical tissue removal, the tissue removal resulting in a body cavity. The method comprises creating access to the cavity, and providing an interstitial brachytherapy apparatus that includes one or more thin-walled tubes, each of said thin-walled tubes being configured to contain one or more radioactive sources. The apparatus further includes at least one radiation source configured to deliver a prescribed dose of radiation, a whisk adjuster configured to permit adjustment of each of the one or more thin-walled tubes so that the tubes substantially conform to a size of the body cavity, an expansion element configured to be engaged to expand outwardly said one or more thin-walled tubes within the cavity so that the thin-walled tubes substantially conform to a shape and/or size of the body cavity, a center core; and wherein, after the expansion element is engaged, the thin-walled tubes are arranged in two substantially concentric circles around the center core. The apparatus further comprises an opening corresponding to each thin-walled tube and/or center core, the opening being configured to permit insertion of the at least one radiation source into each of the one or more thin-walled tubes during or after surgical implantation of the plurality of thin-walled tubes. In accordance with the method, this interstitial brachytherapy apparatus is placed into the cavity, and expanded outwardly so that it substantially conforms to the shape and/or size of the cavity. The method further includes inserting the at least one radiation source into the outwardly expanded thin-walled tubes, clamping the interstitial brachytherapy apparatus onto the patient, leaving the interstitial brachytherapy apparatus inside the cavity for a sufficient time to deliver the prescribed radiation dose to remaining tissue that surrounds the cavity; and removing the interstitial brachytherapy apparatus.

These, as well as other objects, features and benefits will now become clear from a review of the following detailed description of illustrative embodiments and the accompanying drawings.

BRIEF DESCRIPTION OF DRAWINGS

FIGS. 9A and 9B illustrate a bandoleer-configured brachytherapy apparatus in accordance with still yet another embodiment of the present disclosure.

FIG. 10 is an extruded multi-lumen embodiment of a brachytherapy in accordance with still yet another embodiment of the present disclosure.

FIG. 11 is a bendable tube configuration that includes a sleeve configured to slide toward the tubes to reduce the length of the tubes to control the expansion volume.

FIG. 18 is the proximal end portion of a brachytherapy apparatus that includes clamps for each individual tube as well as a clamp for the center tube.

FIG. 19 is the proximal end portion of a brachytherapy apparatus having a key hole-type toggle mechanism for the center tube.

FIG. 20 is the proximal end of a brachytherapy apparatus having a spiral-type spring mechanism used to hold the lumen in place.

FIG. 33D is the brachytherapy apparatus of FIG. 33C with a cutter for removing the portion of the apparatus that is outside of the patient, after implantation of the portion of the brachytherapy apparatus that includes the thin-walled tubes used to deliver radiation to the tissue that remains after the lumpectomy.

DETAILED DESCRIPTION OF ILLUSTRATIVE EMBODIMENTS

Cancer patients are often diagnosed via an initial biopsy. The treating surgeon may then refer the patient to a medical oncologist, who may assist in determining a treatment regimen and inform the patient of various treatment options. In the case of breast cancer, the cancerous tissue is removed via a lumpectomy While the present disclosure is described in terms of breast cancer, it should be understood that the apparatus described in the present disclosure could also be used as part of a wide variety of other treatment regimens, including those for prostate cancer, brain cancer and other situations where a cavity is created by removal of a tumor.

The present disclosure provides a brachytherapy apparatus that delivers a low dose, partial breast irradiation treatment for post-lumpectomy patients via introduction of a catheter-like device through a cannula. The device is designed to be introduced post-surgically with local anesthesia under image guidance into the excision site by a surgeon. For purposes of the present disclosure, low-dose radiation may be construed as a dosage that would allow a patient to receive a prescribed dose if the low-dose radiation source remains in the patient's body over the course of 3, 5 or 7 days.

Figure 1A:
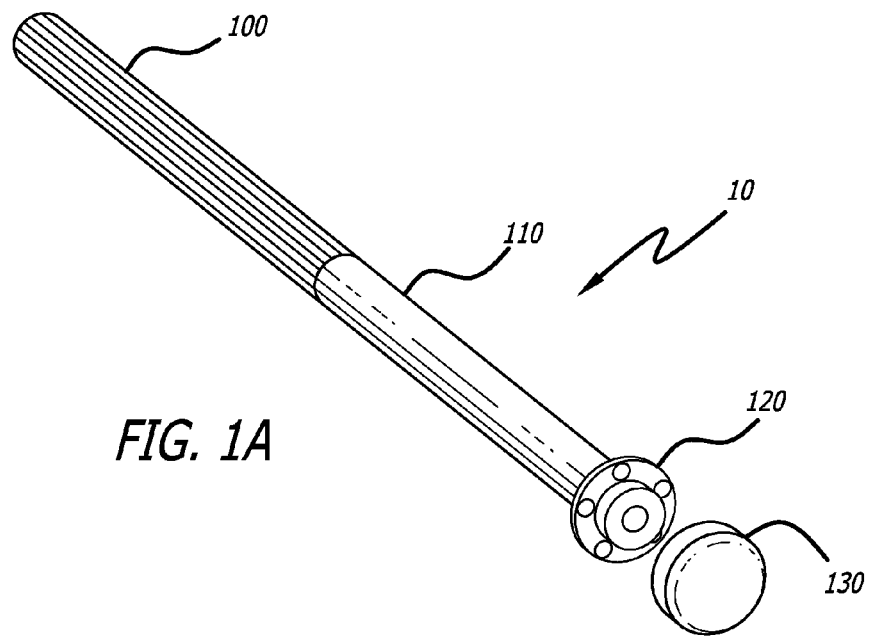
FIG. 1A is a brachytherapy apparatus in a collapsed state in accordance with one embodiment of the present disclosure.

Referring now to FIG. 1A, illustrated is a brachytherapy apparatus 10 in a collapsed state in accordance with one embodiment of the present disclosure. As shown, the apparatus 10 includes a plurality of tubes 100 at its distal end. The tubes 100 are thin-walled. The wall thickness can be as small as between $7/1000$ of an inch and $12/1000$ of an inch. The tubes 100 are disposed within a sleeve 110. Sleeve could simply be thin-walled heat shrink tubing, and the walls of sleeve could be as thin as $3/1000$ of an inch. Each of this plurality of tubes 100 is configured to contain therein a plurality of low-dose radioactive seed strands. The tubes have a distal end and a proximal end, and are bundled together at the distal end and at the proximal end inside sleeve.

The sleeve 110 in which the tubes 100 are disposed is, in turn, passed through disk 120. Disk 120 contains a plurality of openings which may be used to suture the apparatus 10 onto a patient so that the apparatus 10 may be left in the patient's breast or other body part upon completion of the surgical procedure to insert the apparatus 10. At the proximal end of disk 120, also illustrated is cap 130 which may be used to cover the cut ends of the tubes 100 when the patient wears the apparatus 10 after completion of the surgical procedure for implanting the apparatus 10.

When in use, the plurality of tubes 100 of apparatus 10 may be expanded so that the radioactive seeds (not shown) disposed within the tube may be placed more closely to the tissue within the post-lumpectomy cavity.

Figure 1B:
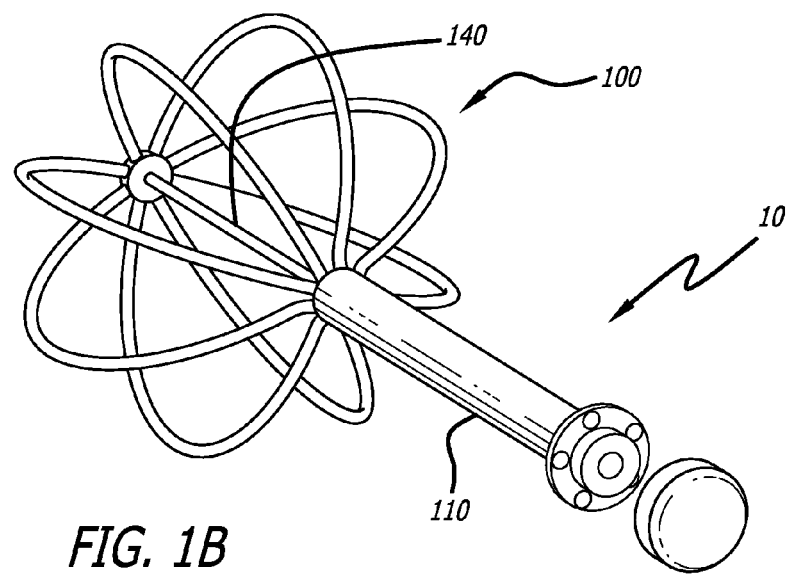
FIG. 1B is an embodiment of the apparatus of FIG. 1A in its expanded state.

Referring now to FIG. 1B, illustrated is an embodiment of the apparatus 10 of FIG. 1A in its expanded state. As shown, the apparatus 10 includes eight (8) tubes 100; however, it should be understood that there may be a greater number of tubes or fewer tubes. The number of tubes may be dependent on a number of factors, including but not limited to, the size of the cavity into which the apparatus 10 is inserted, the amount of radiation needed for the patient and the locations in which the radiation is needed. The size of the cavity as well as the amounts and locations of radiation needed may be determined based on radiation therapy planning, which may be performed using software specifically designed to develop such a radiation plan.

As shown in FIG. 1B, the tubes 100 may expanded to conform to the post-lumpectomy cavity. The size of the sphere may be largely dependent upon the size of the cavity into which the apparatus 10 is inserted. In the embodiment of FIGS. 1A and 1B, the sleeve 110 may be pulled toward the operator so that the tubes 110 expand. An actuator or center tube 140, which extends along the length of the apparatus 10 from its distal end to its proximal end, further assists with expanding and collapsing the apparatus 10.

Figure 2:
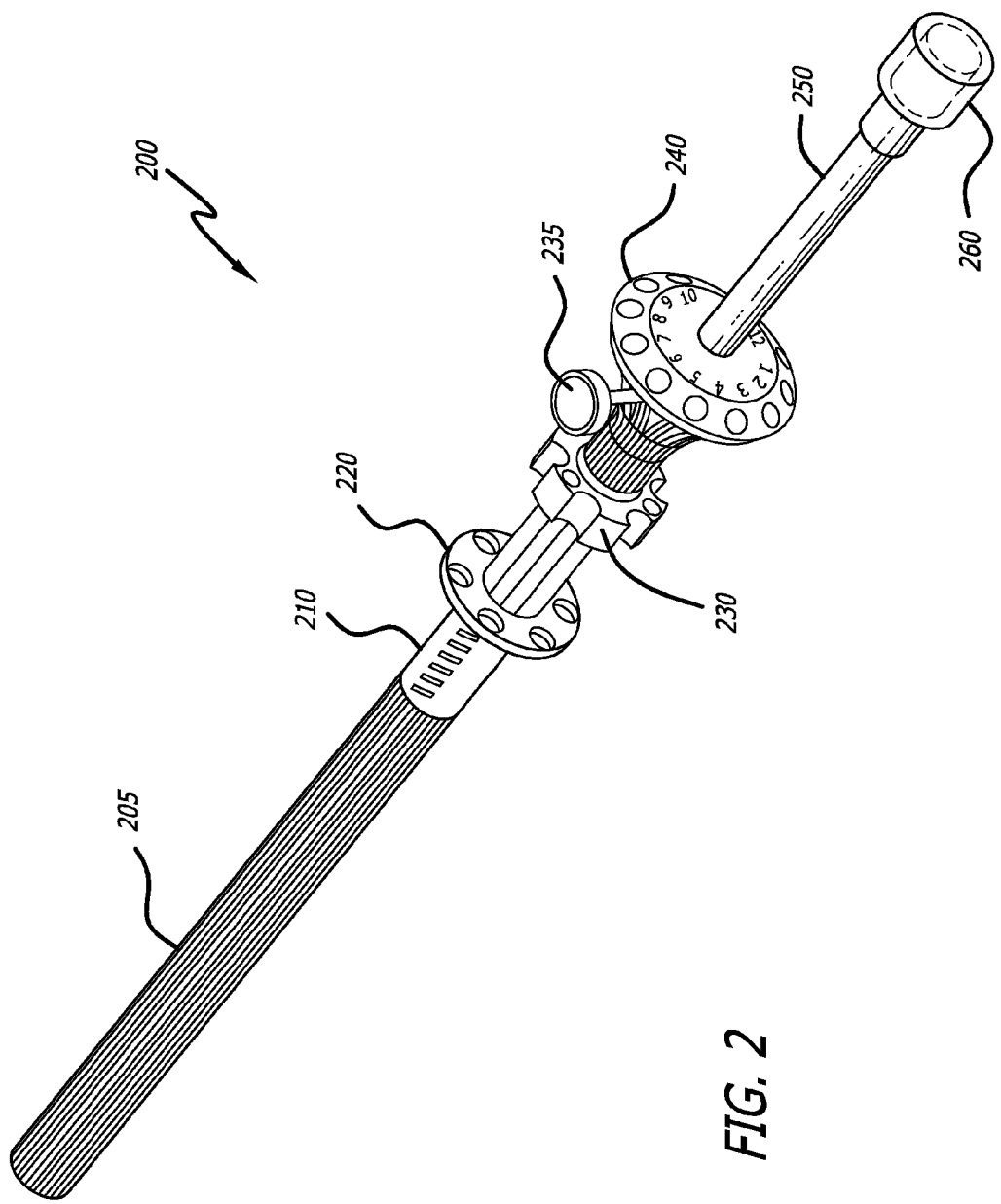
FIG. 2 is a breast brachytherapy apparatus having a clamp and in its collapsed state in accordance with another embodiment of the present disclosure.

Referring now to FIG. 2, illustrated is another embodiment of a breast brachytherapy apparatus 200 in a collapsed state in accordance with a embodiment of the present disclosure.

As shown in FIG. 2, this embodiment 200 includes a plurality of substantially pie-shaped tubes 205, the proximal ends of which are bundled into a collar 210. Collar 210 is connected to disk 220 through which sutures may be disposed in order to suture the apparatus 200 in place once it has been positioned within the patient. The apparatus further includes a conical piece 240 which assists in expansion and also may be used to insert the radioactive seeds, therapeutic elements or diagnostic elements. The seeds may be separated by one or more spacers to create a radioactive seed strand. Lock screw 235 may be used to tighten the center tube 250 and hold the center tube in position with respect to tubes 205. The obturator also assists in expansion and collapse of the apparatus 200, when the obturator is held steady and the conical piece 240 is pushed in.

In operation, first, the physician uses a cannula or trocar to enter the original scar site that was created at the time of the original tumor removal or resection. In the case of the breast, this scar site may have resulted from a lumpectomy.

Figure 3A:
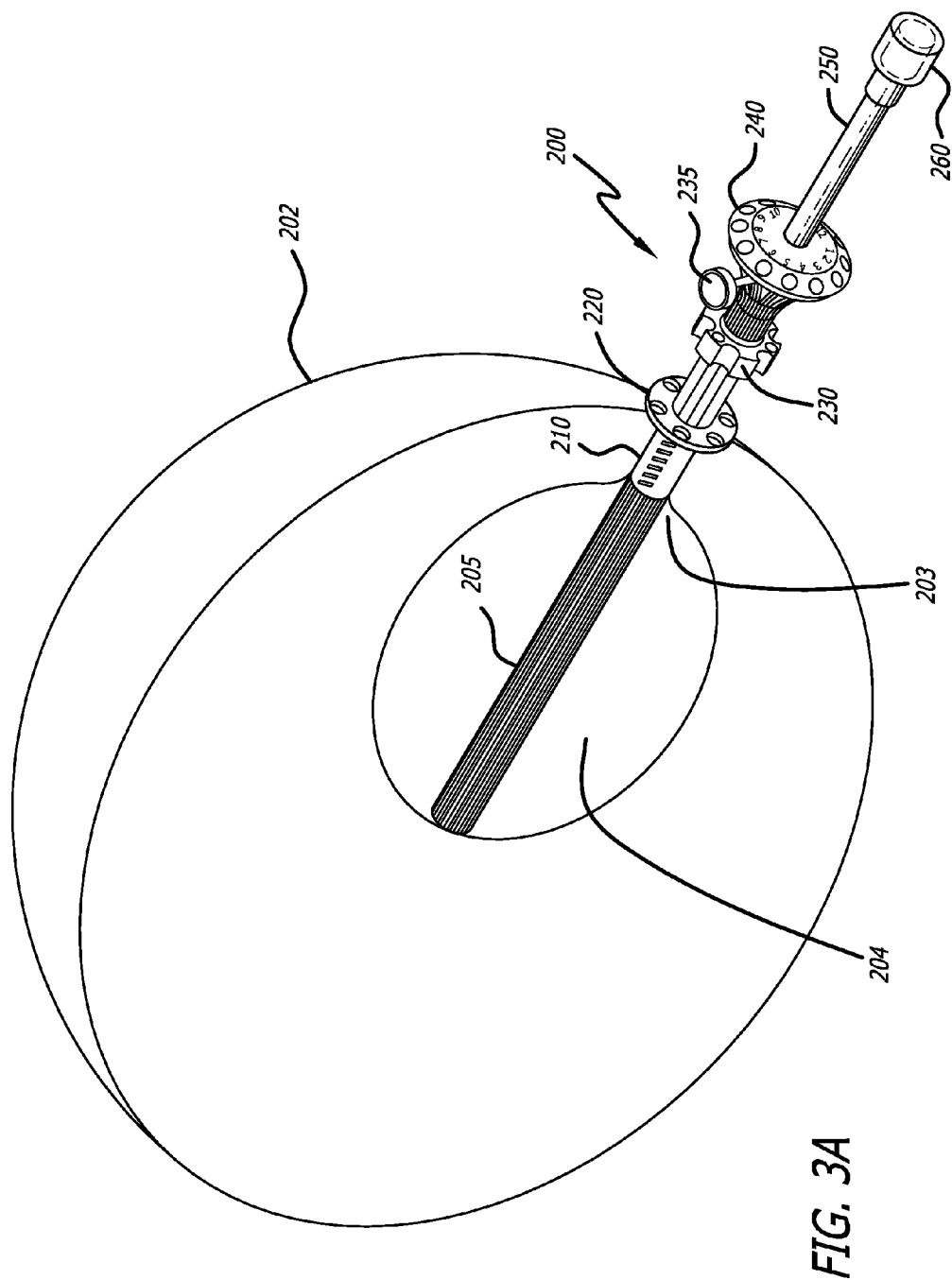
FIG. 3A is the brachytherapy apparatus of FIG. 2 as it is used in a brachytherapy procedure.

Referring now to FIG. 3A, illustrated is the brachytherapy apparatus of FIG. 2 as it is used in a brachytherapy procedure. In a first step, a physician may place the apparatus 200 through the original incision site 203 of the breast 202 that was originally used to perform the lumpectomy. The tubes 205 may be placed into the cavity 204 of the breast 202 that remains after the lumpectomy. Disk 220 is kept outside the patient's breast 202 so that it may be later sutured onto the patient. The clamp 230 will assist with expansion and tightening of the tubes 205.

Figure 3B:
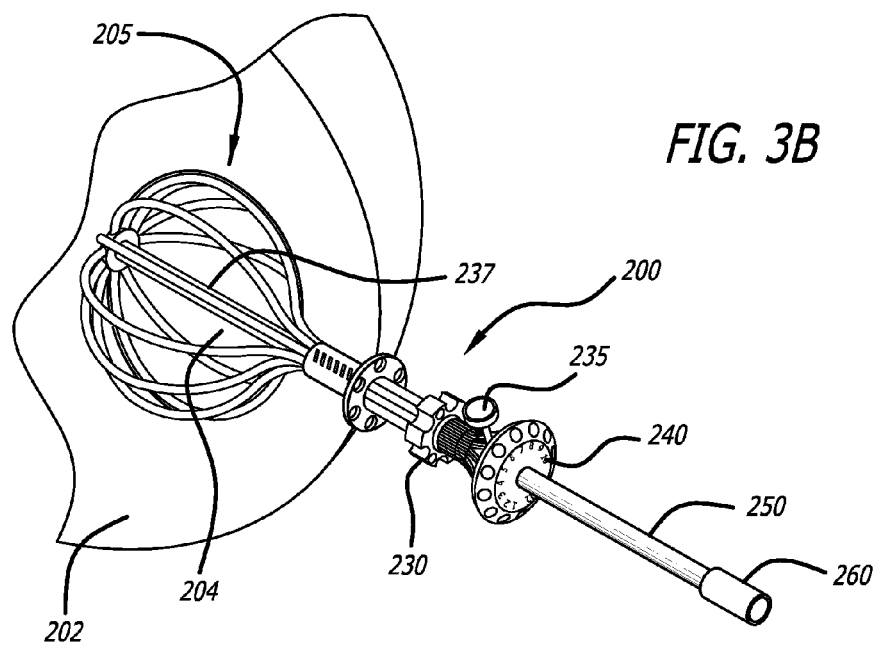
FIG. 3B is the apparatus of FIGS. 2 and 3A in its expanded state in accordance with one embodiment of the present disclosure.

Referring now to FIG. 3B, the apparatus 200 may be expanded much like an umbrella when the physician loosens the lock screw 235, restrains the central tube 250 and pushes member 240 in a distal direction. These motions would cause expansion of the plurality of tubes 205 so that the tubes 205 almost fill the cavity 204 of breast 202.

The physician may use visual and other surgical aids to better assess the position of the tubes 205 inside breast 202. Such aids may be beneficial since the tubes 205 may not be readily seen once they are inside cavity 204. An ultrasound is one such example of visual or surgical aid. The ultrasound may be used to detect the position of the tubes 205 in relation to cavity 204. When the tubes are touching the walls of cavity 204, the physician may see this being illustrated on an ultrasound. In some situations, an ultrasound may not be available. In lieu of—and/or in addition to—using visual or surgical aids, the physician may use his or her senses to determine when resistance is felt resulting from the tubes 205 pushing against the one or more inner surfaces of cavity 204. Once the tubes are against the inner surfaces of cavity 204, the physician may tighten the clamp 230 to hold the position of tubes 205.

Figure 3C:
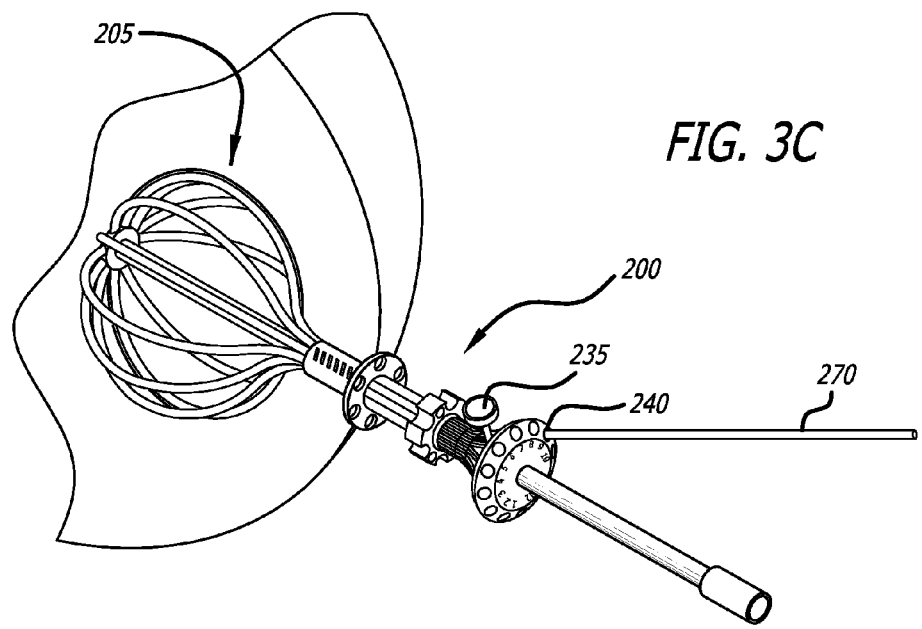
FIG. 3C is the apparatus of FIG. 3B showing the process of radioactive strands being placed into the openings.

Referring now to FIG. 3C, illustrated is the apparatus 200 wherein radioactive seed strands or other therapeutic or diagnostic elements may be placed into tubes 205 through openings located in conical member 240. The openings are numbered, each number corresponding to one of the plurality of tubes 205. Once the tubes 205 are in position, seed strands may be inserted into the tubes via the openings using strand placement tube 270. The openings serve as funnel holes for the tubes.

As mentioned hereinabove, the apparatus of the present disclosure may be suitable for use with common surgical aids. One such surgical aid is a CAT scan which may be used to determine whether the seed strands have been accurately positioned in accordance with the radiation therapy plan. As hereinabove mentioned, the radiation therapy plan may be created with surgical aids such as software designed to form an isodose profile. The appropriate isodose profile may call for the seeds to be inserted in a number of ways so as to vary the applied radiation level. For example, in some situations, the isodose profile may not require that any seed be inserted into one of the plurality of tubes 205. In some situations, two or more different seeds used on a single patient may have different activity levels so that some seeds are stronger than others. Low-dose radioactive seeds, e.g., iodine 125 isotope, may be used in conjunction with breast irradiation.

Under some circumstances, the physician may wish to test proper seed insertion prior to actual insertion by inserting dummy or imitation seeds instead of actual radioactive seeds. This process allows the physician to avoid potentially damaging the real seeds, yet this process may be more time-consuming than placing the actual seeds.

Figure 3D:
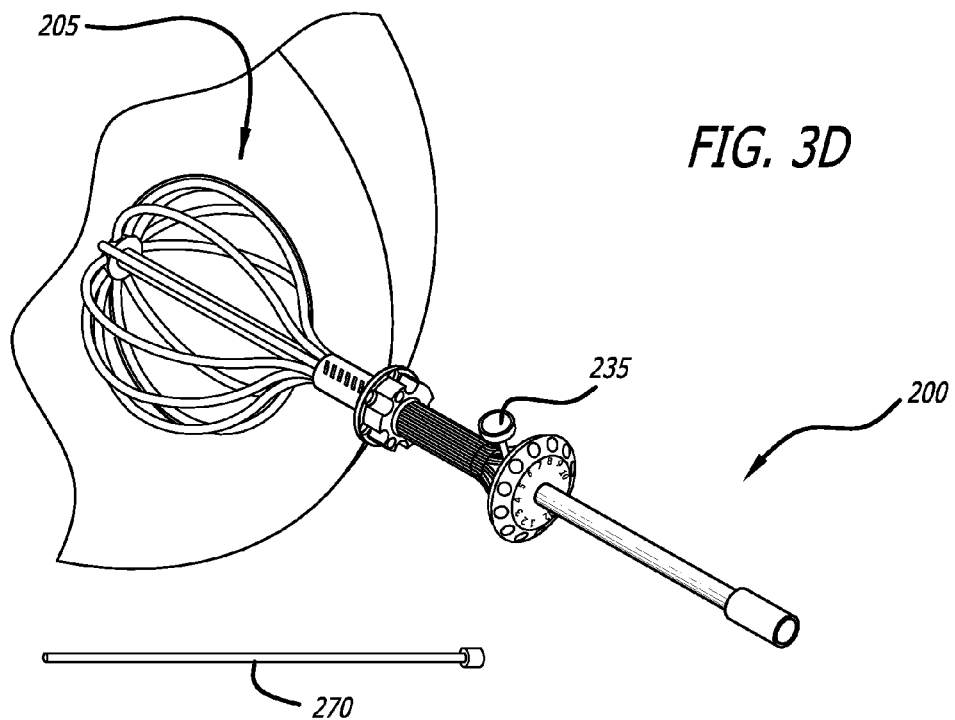
FIG. 3D is the apparatus of FIG. 3C when the tubes are held tightly in place.

Referring now to FIG. 3D, the seed placement tube has been removed and tubes 205 are now held tightly into place with the radioactive seeds having been placed according to the radiation therapy plan.

Figure 3E:
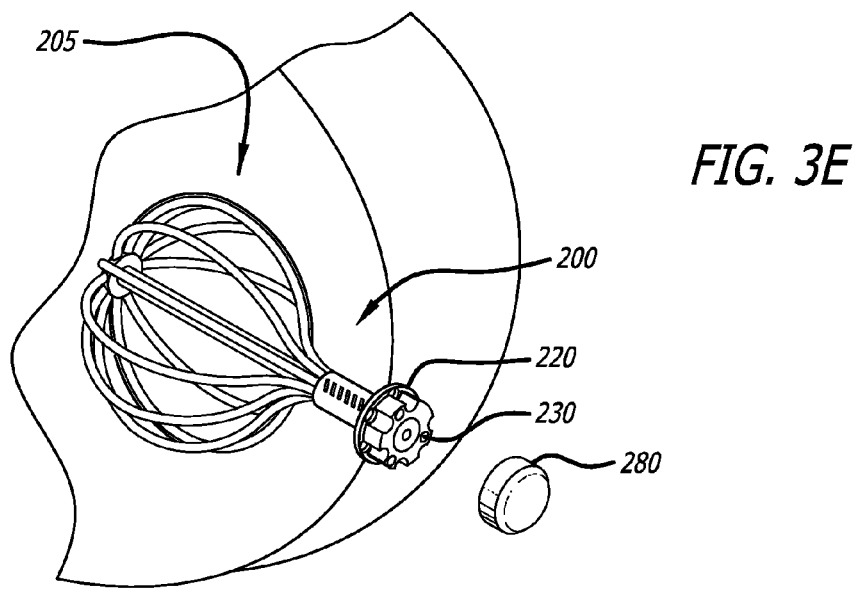
FIG. 3E is a post-implantation embodiment of the brachytherapy apparatus of FIG. 3D.

Referring now to FIG. 3E, illustrated is a post-implantation embodiment of a brachytherapy apparatus 200 of the present disclosure. As shown, the tubes 205 may be cut leaving disk 220 just outside the breast so that the sutures may be disposed through openings in disk 220. The cutting may be performed with a surgical instrument such as a scalpel. Alternatively, the apparatus 200 may be self-cutting using a blade configured to travel across the base of the clamp 230. A cap 280 may be attached to the suture disk to protect the ends of the tubes since the patient may wear the post-implantation apparatus 200 for several days before treatment ends and the apparatus 200 is removed.

Figure 3F:
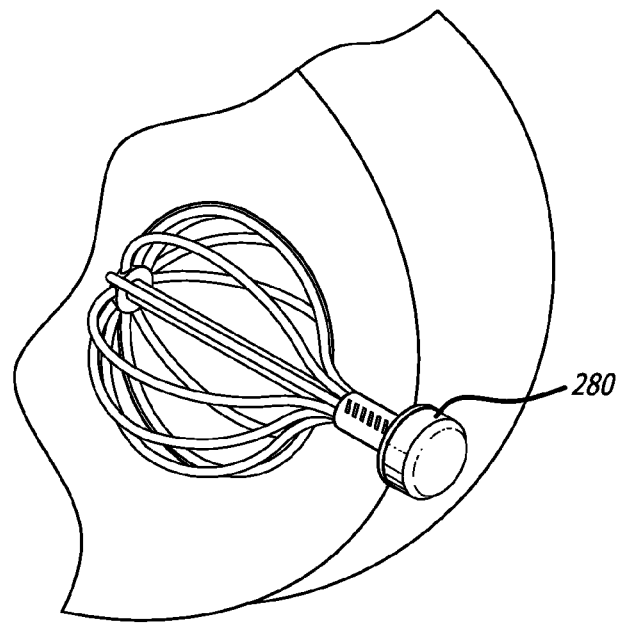
FIG. 3F is a post-implantation embodiment of a brachytherapy apparatus with a post-implantation cap on its end.

Referring now to FIG. 3F, illustrated is the post-implantation embodiment with a post-implantation cap 280 on its end. It is possible that the cap 280 would be secured so that the patient could not remove the cap 280 and disrupt the protocol. At this point, the patient may be sent home with a radiopaque shield (e.g., a lead bra) for several days, e.g., 3-5 days.

Figure 3G:
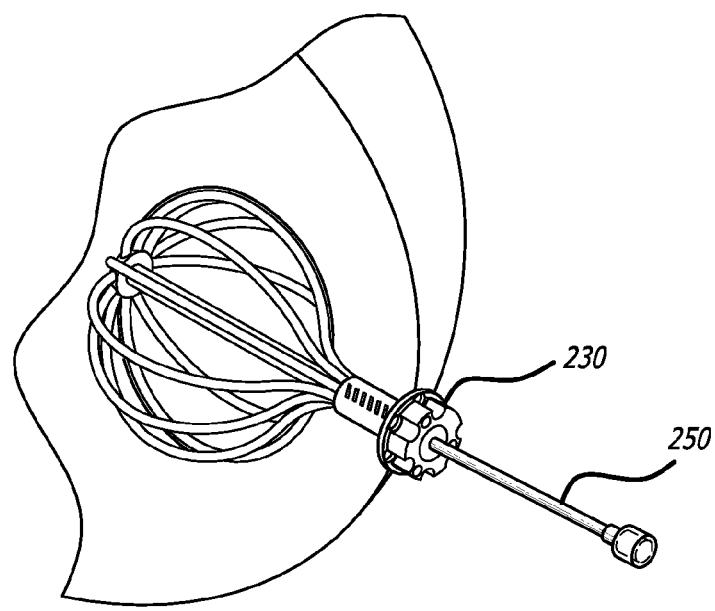
FIG. 3G is an embodiment of a brachytherapy apparatus after an obturator has been inserted.

The apparatus may be removed after a minimum prescribed dose of radiation has been delivered. As shown in FIG. 3G, the cap 280 has been removed and the obturator 260 has been inserted. The clamp 230 would need to be loosened so as to allow the tubes to collapse.

Figure 3H:
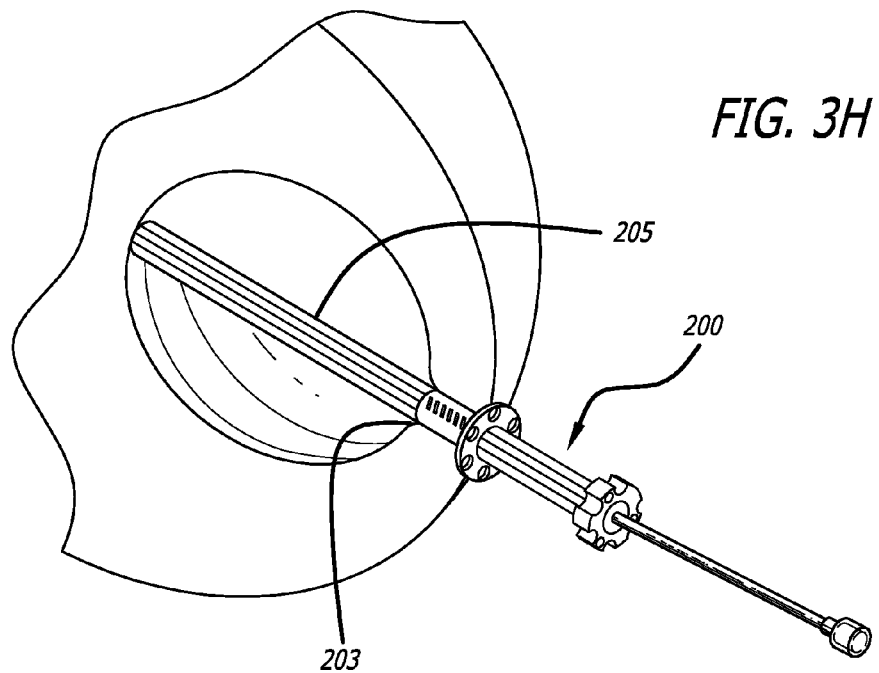
FIG. 3H is an embodiment where the tubes are collapsed.
Figure 3J:
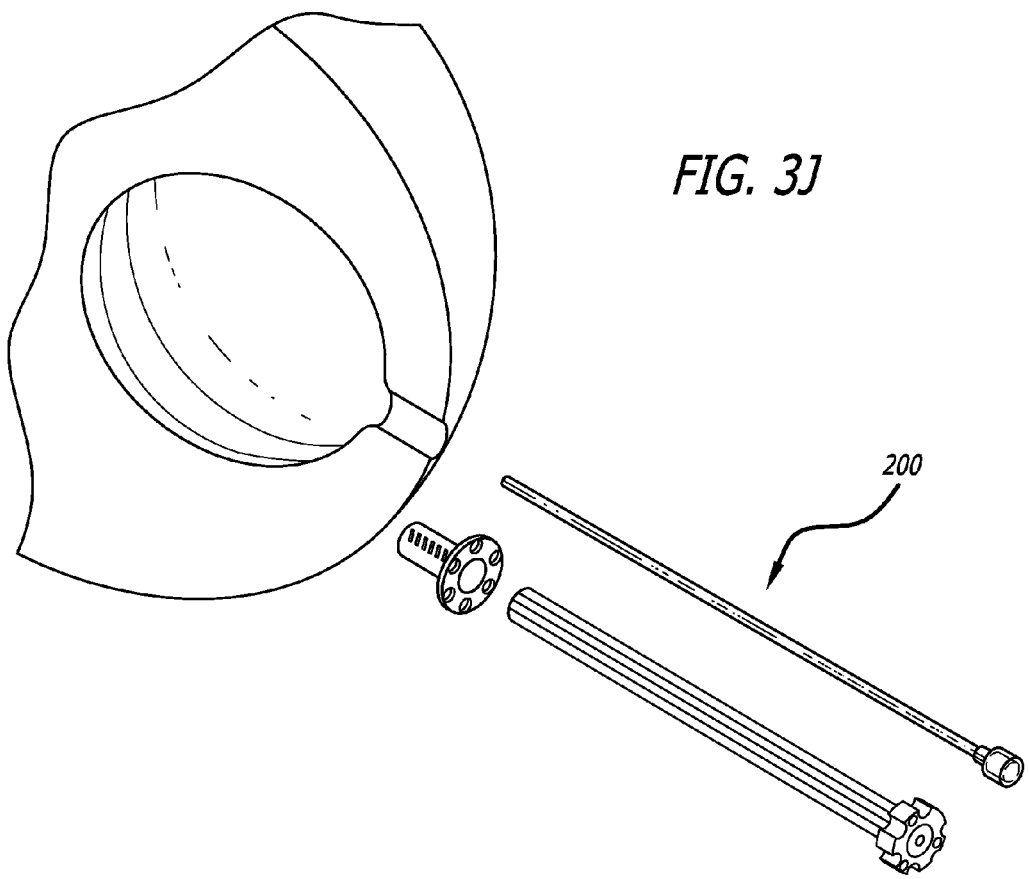
FIG. 3J is an illustration of the apparatus having been removed fully from the breast.
Figure 3I:
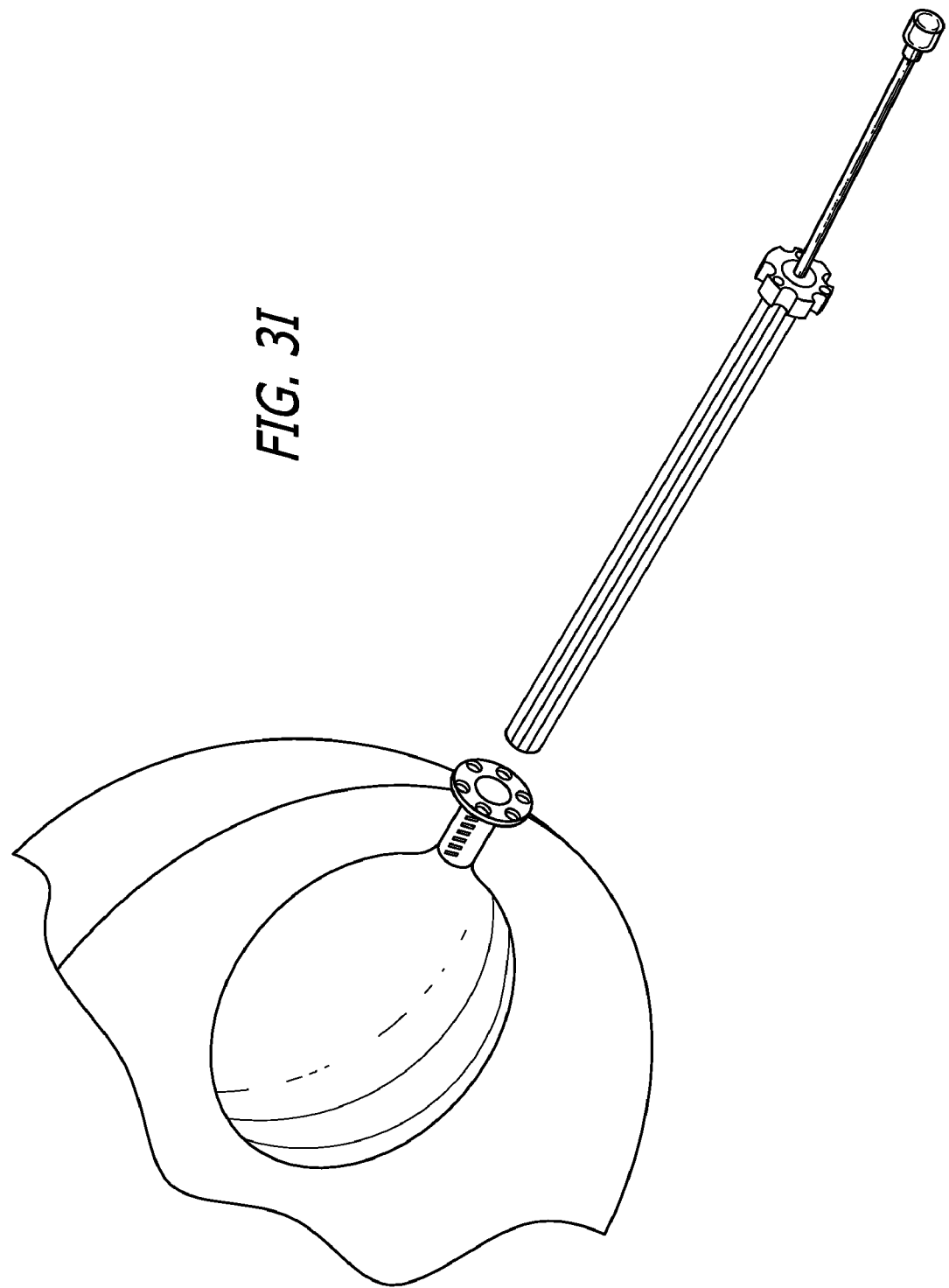
FIG. 3I is an embodiment showing how the brachytherapy apparatus may be removed from a patient, leaving the suture disk in place temporarily.

Referring now to FIG. 3H, the tubes 205 are collapsed. The apparatus 200 may be removed from the site of insertion 203 or other point deemed appropriate by the physician. Referring now to FIG. 3I, the apparatus 200 may be removed from the patient, leaving the suture disk 220 in place temporarily. Referring now to FIG. 3J, the apparatus 200 has been removed fully from the breast.

Figure 4A:
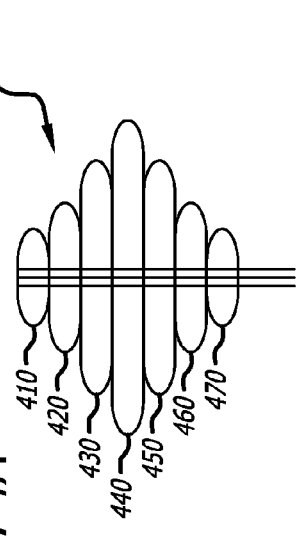
FIG. 4A is the brachytherapy apparatus as stacked, substantially elliptical, expandable tubes and in a collapsed state in accordance with one embodiment of the present disclosure.

Referring now to FIG. 4A, illustrated is the brachytherapy apparatus 400 as stacked, substantially elliptical, expandable tubes and in a collapsed state in accordance with one embodiment of the present disclosure. As illustrated, apparatus 400 includes a plurality of stacked expanding tubes 410, 420, 430, 440, 450, 460 and 470. Uppermost tube 410 is shown above a number of other tubes including middle tubes 430, 440 and lowermost tube 470. The middle tubes 430, 440 have a greater width (w) than uppermost tube 410 and lowermost tube 470.

Figure 4B:
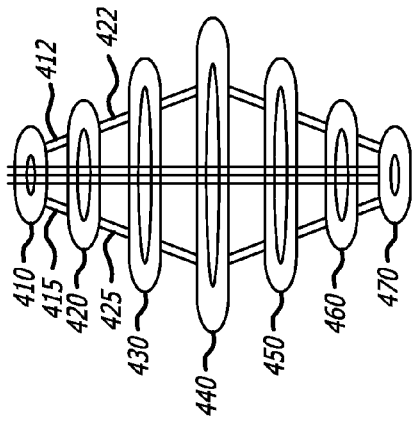
FIG. 4B is the apparatus 4A in its expanded state.

Referring now to FIG. 4B, illustrated is the apparatus 400 of FIG. 4A in its expanded state. Each tube has a top tube section, a middle tube section and a lower tube section. As illustrated, connection mechanisms 415, 417 connect the top tube section of tube 420 to the bottom tube section of tube 410. Likewise, connection mechanisms 425, 427 connect the top tube section of tube 430 to the bottom tube section of tube 420. Connection mechanisms connect the top tube sections of each remaining tube to the bottom tube section of the tube above. However, uppermost tube 410 has no tube above it, and therefore, no connection mechanisms connect the uppermost tube 410 to the bottom tube section of the above it since there is no tube above uppermost tube 410.

Figure 5:
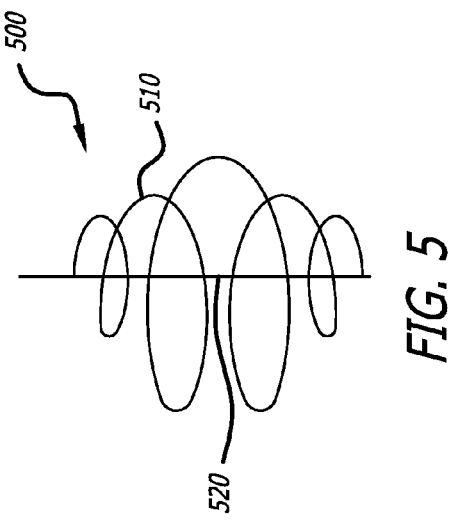
FIG. 5 is a single spiral tube strand brachytherapy apparatus in accordance with another embodiment of the present disclosure.

Referring now to FIG. 5, illustrated is a single spiral tube strand brachytherapy apparatus 500 in accordance with another embodiment of the present disclosure. As illustrated, a single spiral tube strand is wound around a spiral tube support 520. Spiral tube support 520 may be configured to lengthen so that, when lengthened, the spiral tube strand is elongated and expanded to fill a cavity.

Figure 6:
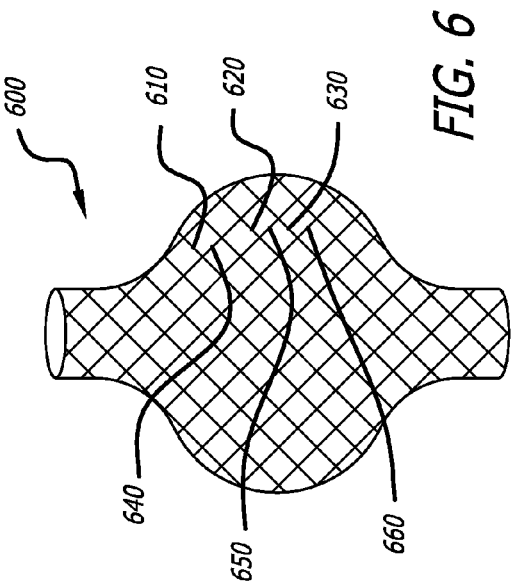
FIG. 6 is an expandable mesh brachytherapy apparatus in its expanded state in accordance with yet another embodiment of the present disclosure.

Referring now to FIG. 6, illustrated is an expandable mesh brachytherapy apparatus 600 in its expanded state in accordance with yet another embodiment of the present disclosure. As illustrated, the apparatus 600 includes a plurality of tubes that are configured in a first direction. For example, tubes 610, 620 and 630 extend diagonally from a northwesterly direction to a southeasterly direction. A second set of tubes are configured in a second direction. For example, tubes 640, 650 and 660 extend from a northeasterly direction to a southwesterly direction such that tubes 640, 650 and 660 intersect with tubes 610, 620 and 630. Radioactive seeds or other therapeutic elements are disposed within the plurality of tubes. The diameter of apparatus 600 is greater in the middle section than in the upper and lower sections.

Figure 7A:
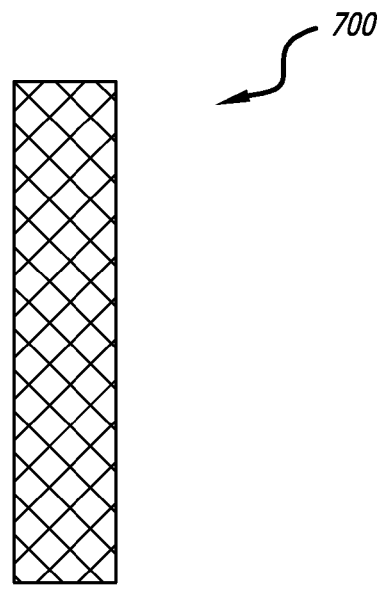
FIGS. 7A and 7B illustrate a stent embodiment of a brachytherapy apparatus in a collapsed and expanded state in accordance with still yet another embodiment of the present disclosure.

Referring now to FIG. 7A, illustrated is a stent embodiment of a brachytherapy apparatus 700 in a collapsed state in accordance with still yet another embodiment of the present disclosure. As illustrated, a plurality of tubes are interconnected to define a conical shape when the tube is in its collapsed state.

Figure 7B:
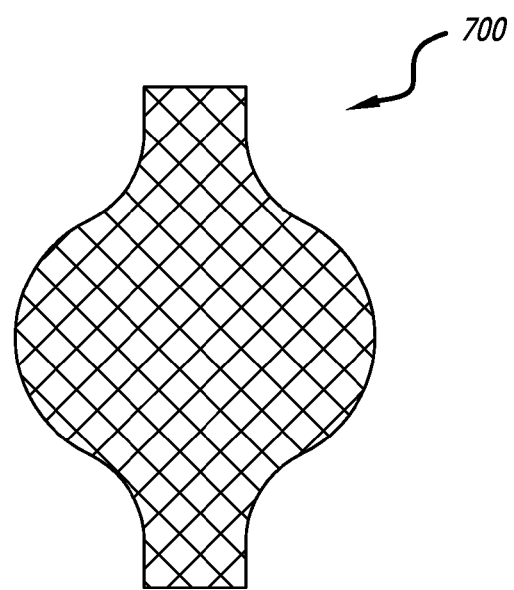

Referring now to FIG. 7B, illustrated is the stent embodiment of FIG. 7A in an expanded state. As illustrated the diameter of 700 is greater in the middle section than in the upper and lower sections.

Figure 8:
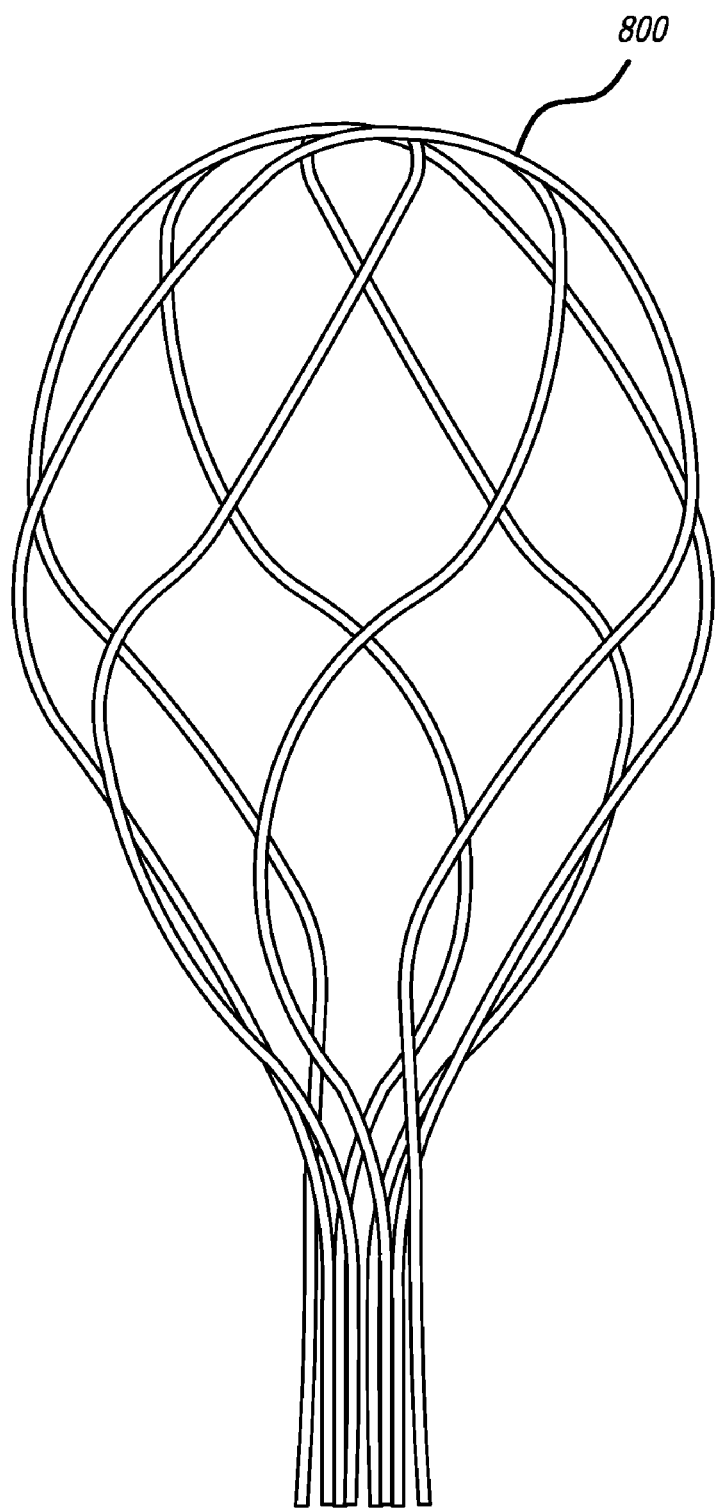
FIG. 8 is a multi-tube spiral embodiment of a brachytherapy apparatus in accordance with still yet another embodiment of the present disclosure.

Referring now to FIG. 8, illustrated is a multi-tube spiral embodiment of a brachytherapy apparatus 800 in accordance with yet another embodiment of the present disclosure. As shown, the apparatus 800 includes a plurality of tubes that spiral in the same direction. The tubes are joined at the top and converge near the bottom.

Referring now to FIG. 9A, illustrated is a bandoleer-configured brachytherapy apparatus in accordance with still a further embodiment of the present disclosure. As illustrated, multiple expandable ribbons with cross tubes attached 910, 920 and 930 are configured to contain a plurality of seeds or other therapeutic elements. The cross tube ribbons 910, 920, 930 are threaded through a tube 940 into the cavity. FIG. 9B illustrates how radioactive seeds 922, 924, 926, 928 or other therapeutic elements may be inserted into the cross tubes 920.

At times, a brachytherapy apparatus may need to be re-sized to fill the cavity that remains after a surgical resection. It may also be desirable that this re-sizing is performed by the surgeon who is also responsible for implanting the brachytherapy apparatus into a patient. It may be further desirable that the tube bundle be rigid in order to facilitate insertion.

Referring now to FIG. 10, illustrated is an extruded multi-lumen embodiment of a brachytherapy apparatus 1000 in accordance with yet another embodiment of the present disclosure. As illustrated, webs 1010 hold tubes together in collapsed state, when tube expanded could be slit to the length required so that the tubes may be individually presented. The apparatus 1000 could be manufactured to include the slit webs 1010, and the length of the slits could correspond to the size of a particular sphere 1020 of the apparatus 1000. Alternatively, the surgeon could perform this slitting process. Moreover, a special cutter could be provided for the tubes, or the tubes could be marked or gauged to determine the appropriate length.

Other means may be provided in order to control the length of the tubes in the brachytherapy apparatus so that different cavity sizes are accommodated. Referring now to FIG. 11, illustrated is a bendable tube configuration that includes a sleeve 1110 configured to slide toward the tubes 1120 to reduce the length of the tubes, thus accommodating smaller cavities. The sleeve 1120 may be slid toward disk 1130 to lengthen the tubes 1120, thus accommodating larger cavities. If the tubes 1120 are shortened, it may be desirable to cut any exposed portion of the tubes 1120 extending from end section 1140 or sleeve 1110.

Figure 12:
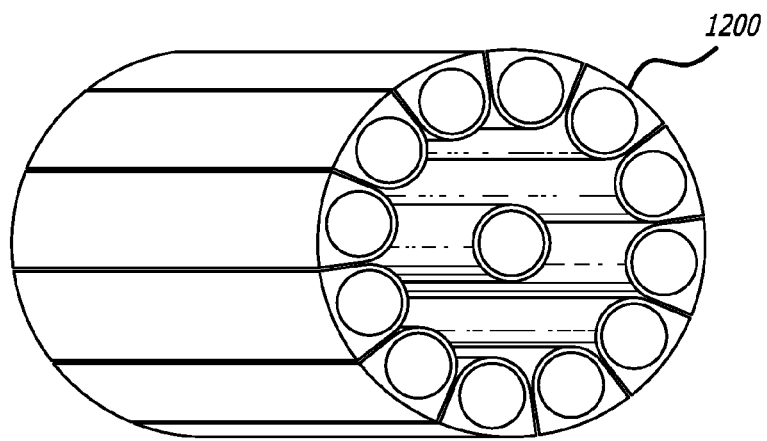
FIG. 12 is a multi-lumen brachytherapy apparatus having tubes that are snugly fit from side-to-side.

A multi-lumen tube could also be configured so that its tubes fit side-to-side when the tube is in its collapsed state. Such an embodiment could enhance stability of the apparatus. Referring now to FIG. 12, illustrated is a multi-lumen brachytherapy apparatus 1200 having tubes that are snugly fit from side-to-side.

Figure 13:
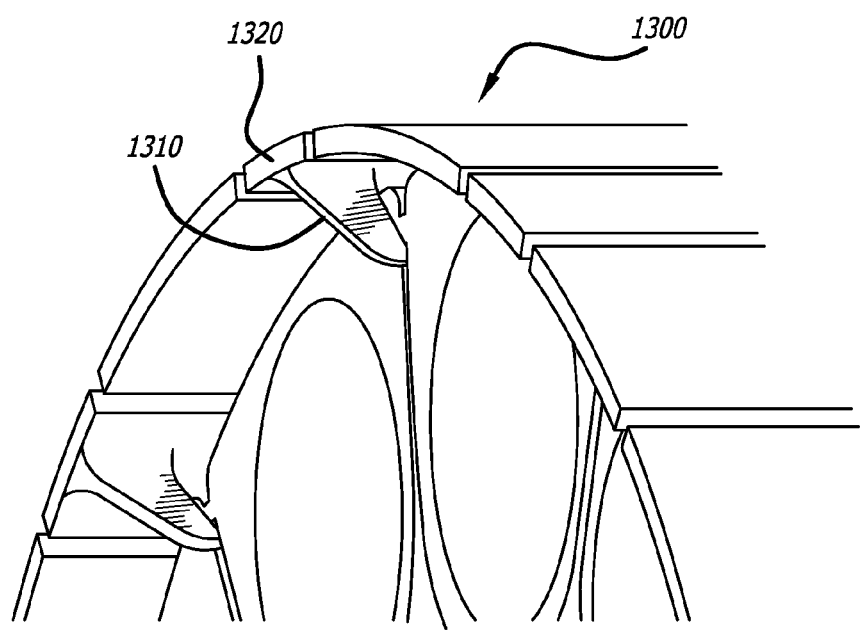
FIG. 13 is a multi-lumen tube that could also be configured for expansion at the time of use through the use of molded "knives" at the interior surface of a sleeve of the apparatus.

Referring now to FIG. 13, a multi-lumen tube could also be configured for expansion at the time of use through the use of molded "knives" 1310 at the interior surface of a sleeve 1320 of the apparatus 1300.

Figure 14A:
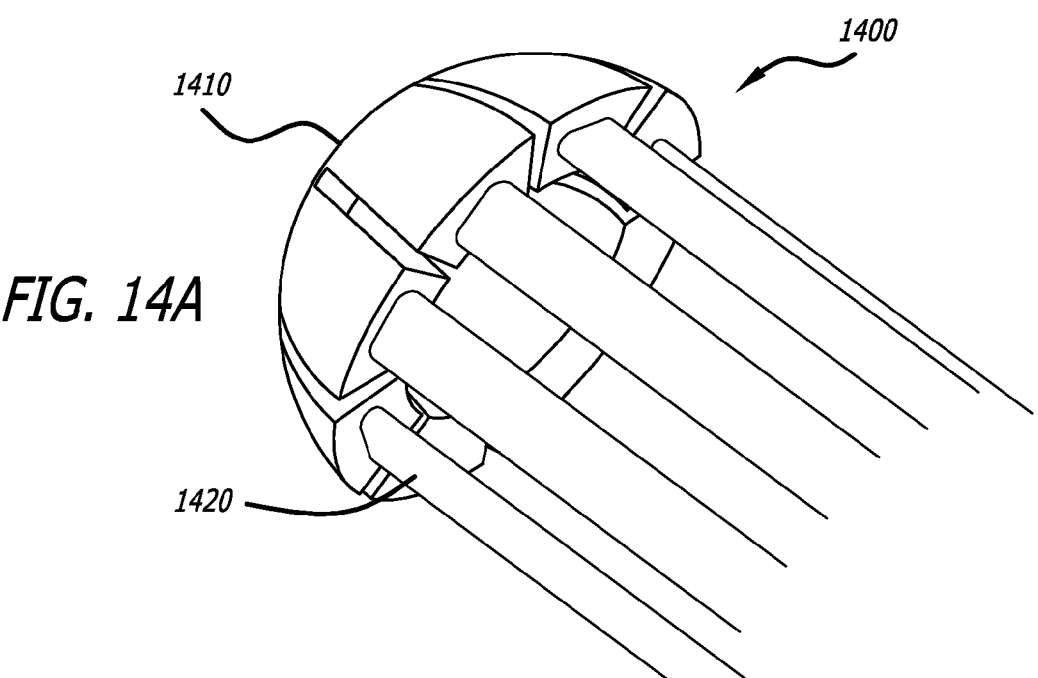
FIG. 14A is a side view of a brachytherapy apparatus that includes a cap joined to the tubes.

To further facilitate spherical expansion inside the tubes, the tubes may be molded or welded to a cap. Referring now to FIG. 14A, illustrated is a side view of a brachytherapy apparatus 1400 that includes a cap 1410 joined to the tubes 1420. Cap 1410 may be molded or welded to the tubes 1420 in order to facilitate spherical expansion of the tubes 1420.

Figure 14B:
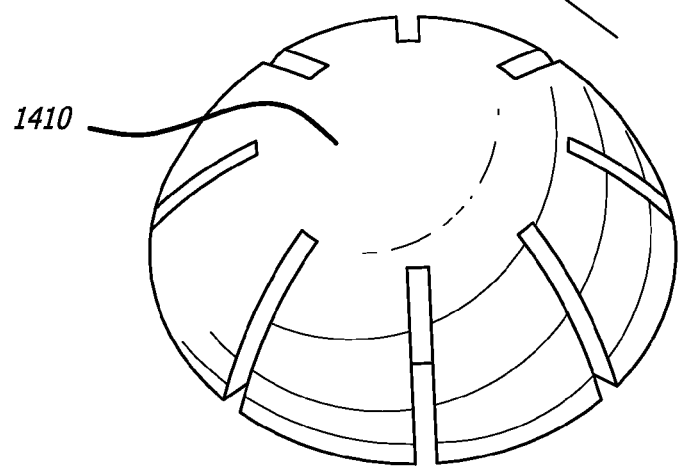
FIG. 14B is a top view of the cap described in FIG. 14A.
Figure 14C:
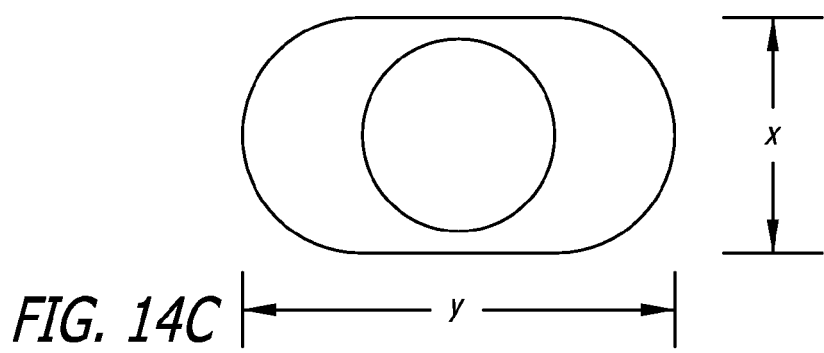
FIG. 14C is a dimensional representation of the cross section of the tubes of FIG. 14A.

Referring now to FIG. 14B, illustrated in a top view of the cap 1410 described in FIG. 14A. As shown, the cap 1410 has a smooth surface that could further facilitate insertion of the apparatus 1400 into the cavity of a patient when in use. Referring now to FIG. 14C, illustrated is a dimensional representation of the sphere formed by one of the tubes 1420 of FIG. 14A. In order to control the bend radius of the a tube through which the radioactive seeds or other therapeutic elements will pass, the x dimension could be increased or decreased. To gain greater control over expansion by keeping the tubes equally distributed radially, the y dimension may be adjusted. This sizing will affect the catheter size and the maximum diameter depending upon the maximum distance between the seeds allowable to maintain the appropriate prescribed dose.

Figure 15:
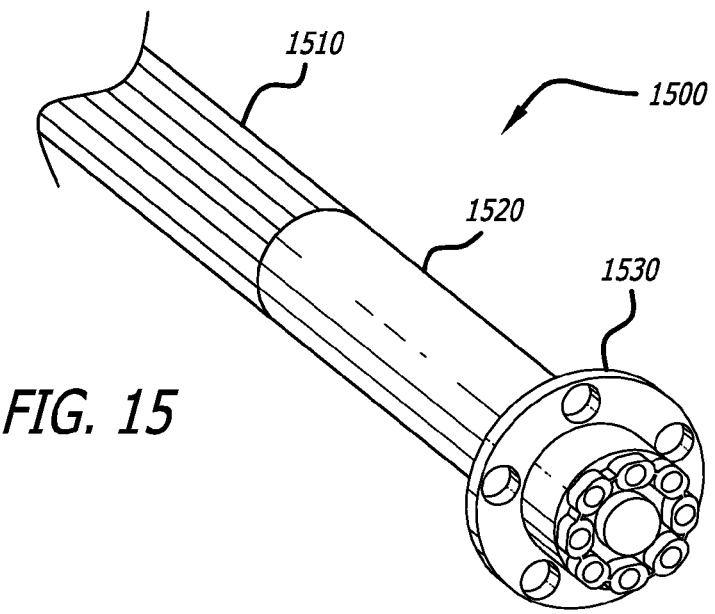
FIG. 15 is a dual-sleeved proximal end portion of a brachytherapy apparatus in accordance with one embodiment of the present disclosure.

Referring now to FIG. 15 illustrated is a dual-sleeved proximal end portion of a brachytherapy apparatus 1500 in accordance with one embodiment of the present disclosure. This proximal end portion has two sleeves 1510, 1520 with sleeve 1510 adapted to be slid proximally toward disk 1530. Accordingly, sleeve 1510 could be slid into, and thus disposed inside, sleeve 1520 to lengthen any attached tubes, thus accommodating a larger cavity.

Figure 16:
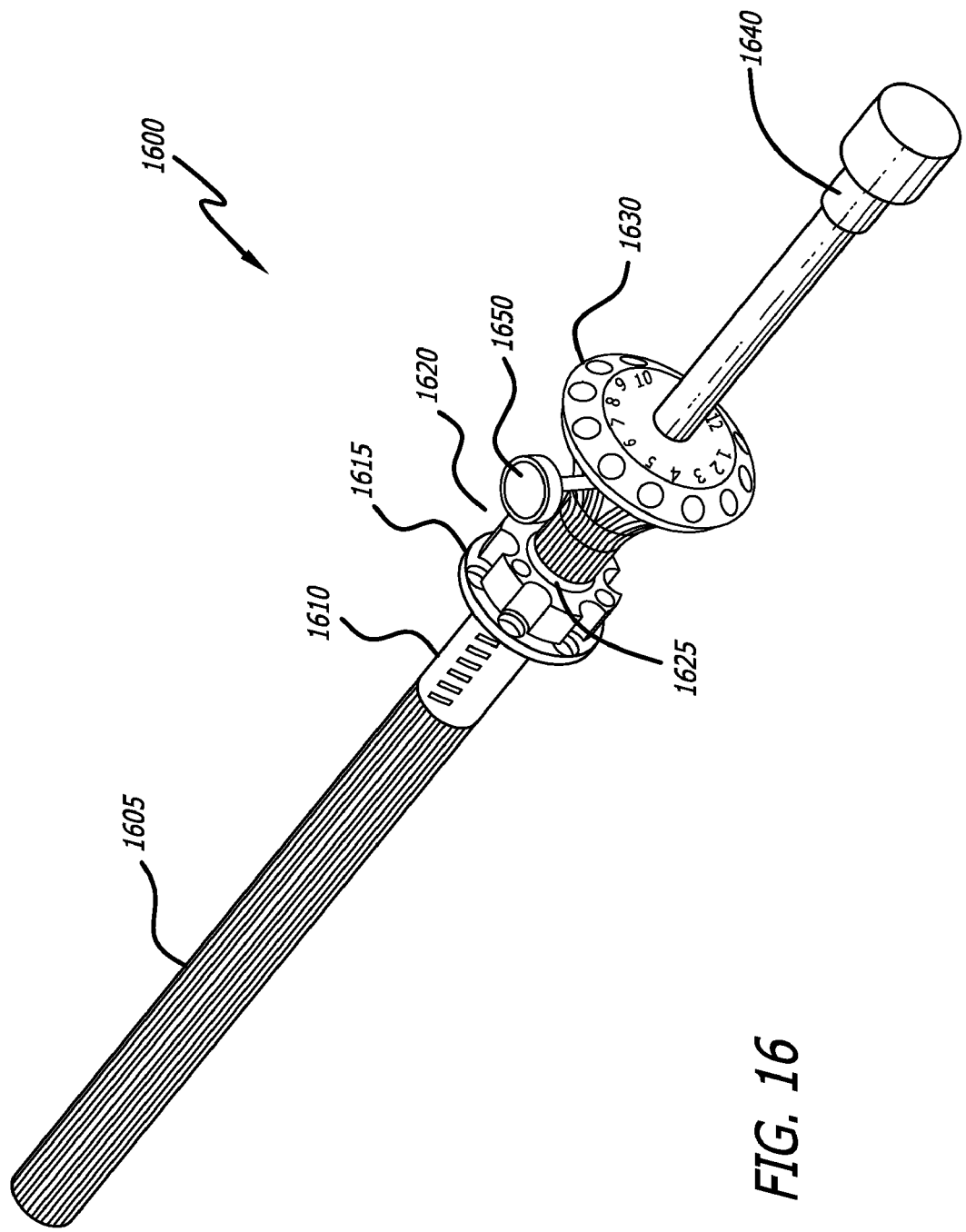
FIG. 16 is a brachytherapy apparatus having a threaded sleeve and clamp in accordance with another embodiment of the present disclosure.

Referring now to FIG. 16, illustrated is a brachytherapy apparatus 1600 having a threaded sleeve and clamp in accordance with another embodiment of the present disclosure. As illustrated, the apparatus 1600 includes a threaded sleeve 1610 adapted to receive a plurality of tubes 1605. The sleeve 1605 protects the tissue against pressure when the tubes 1605 need to be opened up. If desired, a physician performing brachytherapy could cut the sleeve to the desired size or the sleeves could be manufactured to a certain length. At the proximal end of disk 1615, just proximal to clamp 1620, sleeve portion 1625 can be seen as it protrudes from clamp 1620. Clamp 1620 squeezes tubes. An obturator is placed into hole of center tube and physically connected to the luer fitting on the end of tube 1640. Lock screw 1650 can be used to hold the center tube in place. General operation of this apparatus is similar to that shown in FIG. 2.

Figure 17:
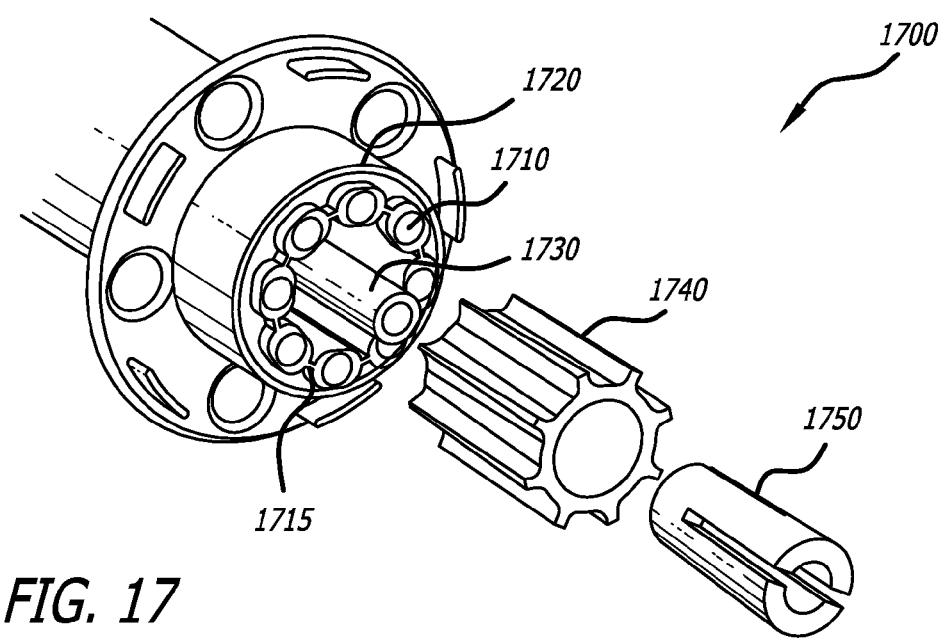
FIG. 17 is the proximal end portion of a brachytherapy apparatus that includes a tapered wedge and collet in accordance with another embodiment of the present disclosure.

Referring now to FIG. 17, illustrated is the proximal end portion of a brachytherapy apparatus 1700 that includes a tapered wedge and collet in accordance with another embodiment of the present disclosure. The tapered wedge and collet may be used to secure the eight-lumen tube 1710 and center tube 1730 to the apparatus. As shown, an eight-lumen tube 1710 having webs, such as web 1715, protrudes from sleeve 1720. Center tube 1730 can be seen extending from the middle of the eight-lumen tube 1710. Tapered wedge could be inserted on the inside diameter of sleeve 1720 to secure the eight-lumen tube 1710. The collet 1750 could be used to secure the center tube 1730. Once secured, the center tube 1730 would be clamped into place by collet 1750.

Referring now to FIG. 18, illustrated is the proximal end portion of a brachytherapy apparatus 1800 that includes clamps for each individual tube as well as a clamp for the center tube. The center tube 1810 may be clamped by squeezing center tube 1820 using forceps or other devices so that center tube clamp structure 1815 holds center tube 1810 into place. Each individual clamp may be clamped using individual tube spring member 1830 to hold the individual clamp in individual clamp structure 1840. When this spring member 1830 is squeezed, it releases the tube in place.

Referring now to FIG. 19, illustrated is the proximal end portion of a brachytherapy apparatus 1900 having a key hole type toggle mechanism for the center tube. The key hole-type toggle mechanism 1910 would be turned in one direction to clamp the center tube in place. The toggle mechanism would be turned in a second direction to unclamp the center tube.

Referring now to FIG. 20, illustrated is the proximal end of a brachytherapy apparatus 2000 having a spiral-type spring mechanism used to hold the lumen in place. The spiral-type spring mechanism 2010 could be released to collapse the brachytherapy apparatus 2000.

Figure 21:
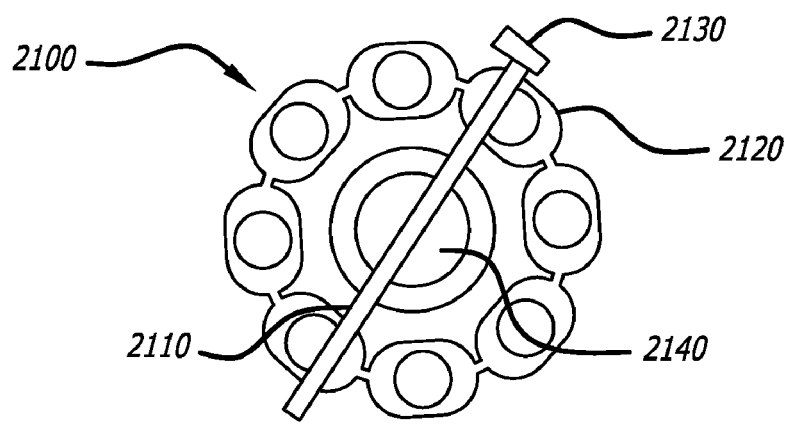
FIG. 21 is the proximal end of a brachytherapy apparatus having a pin mechanism used to hold the lumen in place.

Referring now to FIG. 21, illustrated is the proximal end of a brachytherapy apparatus 2100 having a pin mechanism used to hold the lumen in place. The pin mechanism 2110 could be inserted through a web 2130 of the eight-lumen tube 2120 and through the center tube 2140 to hold the center tube in place as well.

Figure 22:
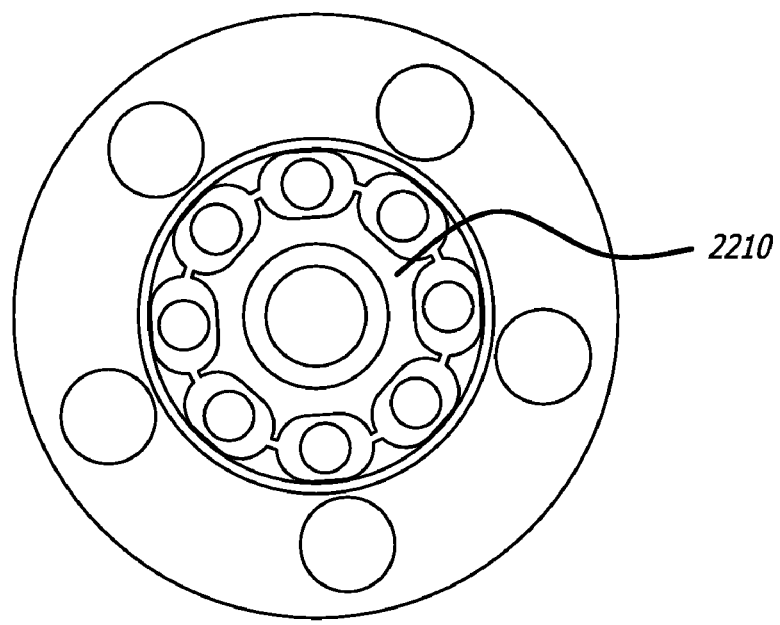
FIG. 22 is another view of a proximal end of a brachytherapy apparatus having a collet system similar to that shown in FIG. 17.

Referring now to FIG. 22, illustrated is another view of a proximal end of a brachytherapy apparatus 2200 having a collet system similar to that shown in FIG. 17. The collet 2210 may be ribbed so that pressure is applied only to the web of the lumen tube. This would leave the inside diameter undistorted so that the radioactive seeds or strands may pass freely.

Figure 23:
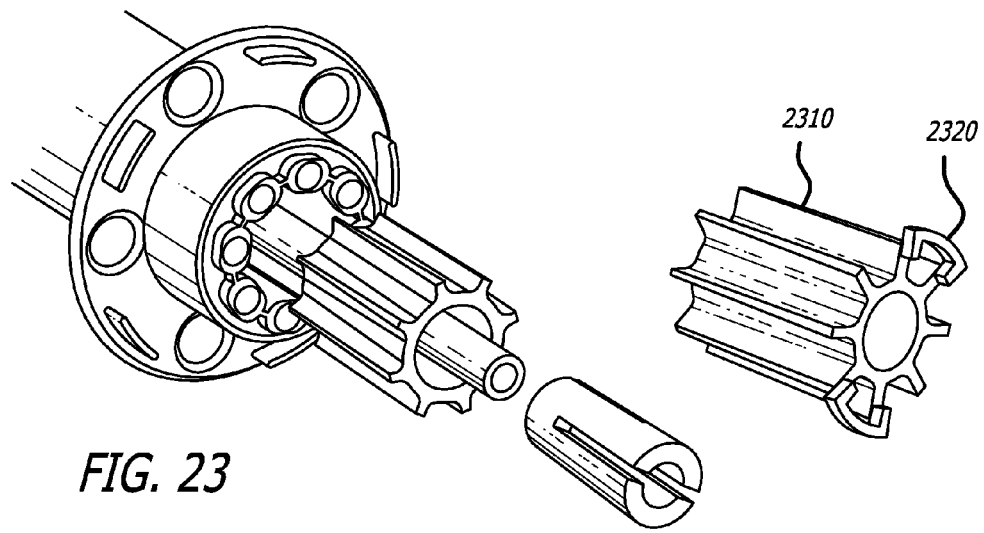
FIG. 23 is also another view of a proximal end of a brachytherapy apparatus having a collet system similar to that shown in FIG. 17.

Referring now to FIG. 23, illustrated is another view of a proximal end of a brachytherapy apparatus 2200 having a collet system similar to that shown in FIG. 17. However, in this embodiment, the collet 2310 includes a handle 2320 so that the collet 2310 may be released.

Figure 24:
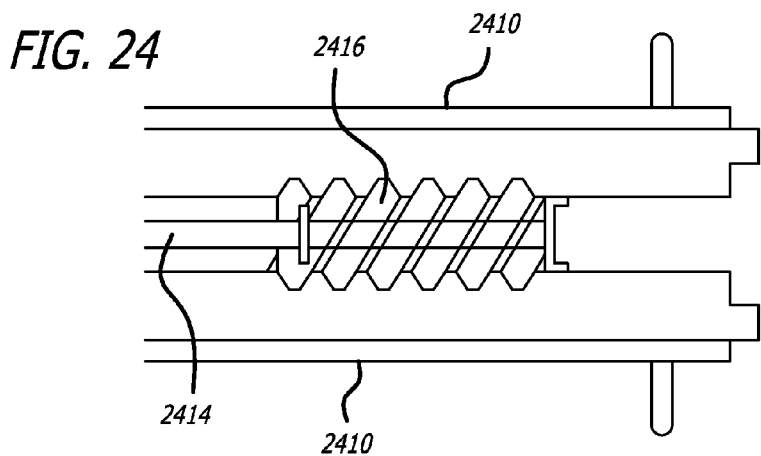
FIG. 24 is another view of a proximal end of a brachytherapy apparatus having a screw mechanism for expanding and collapsing the brachytherapy tubes.

Referring now to FIG. 24, illustrated is yet another view of a proximal end of a brachytherapy apparatus having a screw mechanism for expanding and collapsing the brachytherapy tubes. As shown, between the outer set of tubes 2410 and 2412, the center tube 2414 may be held in place with screw 2416. When the screw 2416 is turned to move in a distal direction, the center tube 2416 is advanced so that the outer sets of tubes 2410, 2412 expand. When the screw 2416 is turned to move in a proximal direction, the center tube 2416 recedes so that the outer sets of tubes 2410, 2412 collapse.

Figure 25:
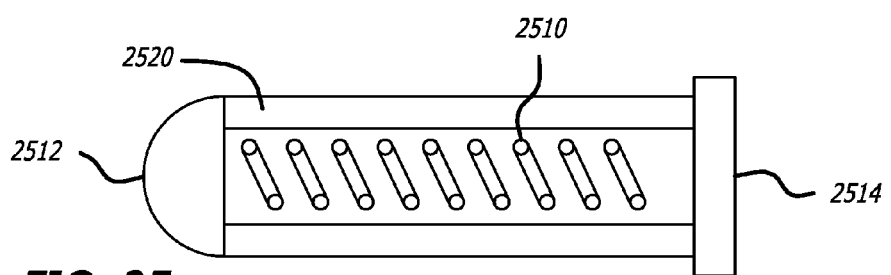
FIG. 25 is still another view of a proximal end of a brachytherapy apparatus having a spring mechanism for expanding and collapsing the brachytherapy tubes.

Referring now to FIG. 25, illustrated is still another view of a proximal end of a brachytherapy apparatus having a spring mechanism for expanding and collapsing the brachytherapy tubes. At one end, the spring mechanism 2510 may be attached to cap 2512, while at the other end, spring mechanism 2510 may be attached to suture disk 2514. The spring mechanism 2510 may be pulled to expand the tubes 2520. The spring mechanism 2510 may be pushed to release the tubes 2520.

Figure 26A:
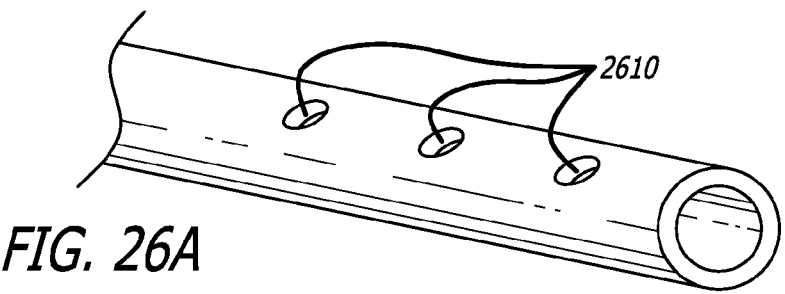
FIGS. 26A and 26B illustrate an embodiment of a split nut and bump configuration used to hold a center tube in place.
Figure 26B:
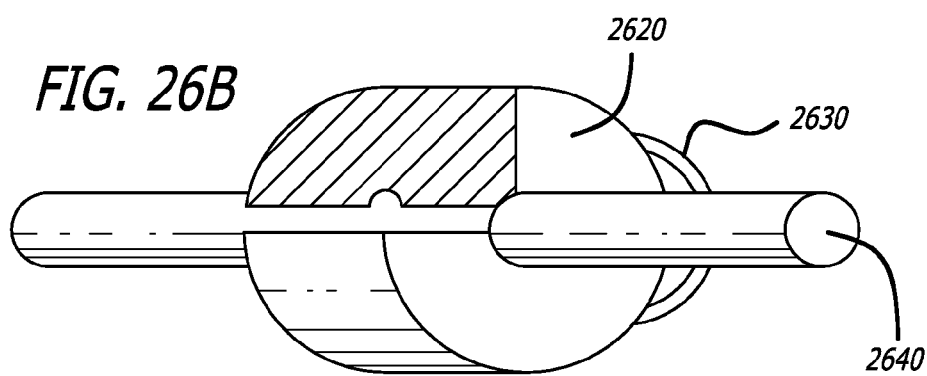

Referring now to FIG. 26A, illustrated is a center tube having bumps 2610 to facilitate holding the center tube in place. As shown in FIG. 26B, the bumps may fit into a split nut 2620 joined by a handle 2630 to hold the center tube 2640 in place.

Figure 27A:
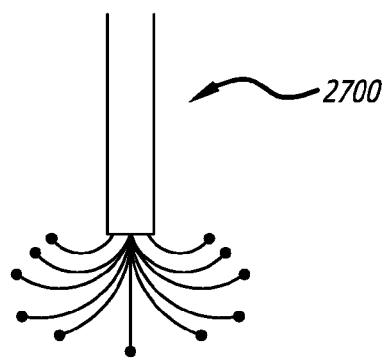
FIGS. 27A and 27B illustrate a brachytherapy apparatus having a ball of seeds at its end.
Figure 27B:
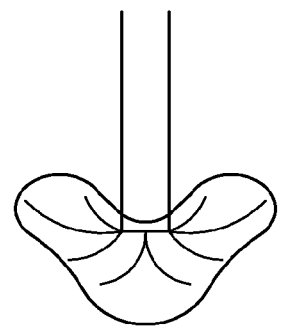

Referring now to FIG. 27A, illustrated is a brachytherapy apparatus 2700 having a ball of seeds at its end. The apparatus is shown in FIG. 27B is shown as it is inserted into a cavity.

Figure 28A:
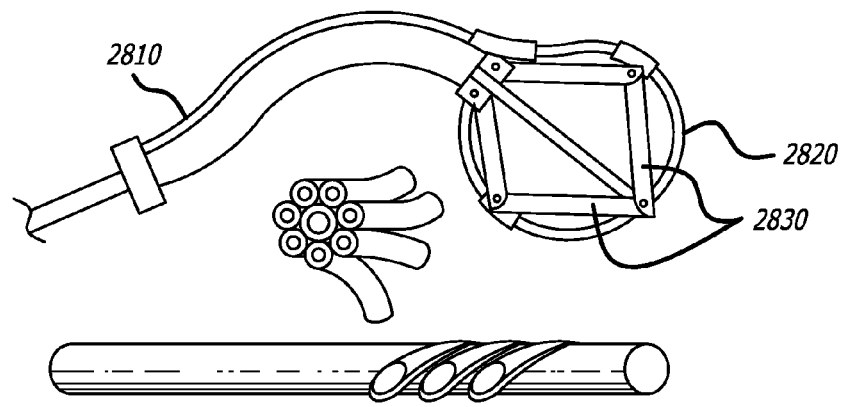
FIG. 28A is another embodiment of a brachytherapy apparatus that includes supports for the tubes.
Figure 28B:
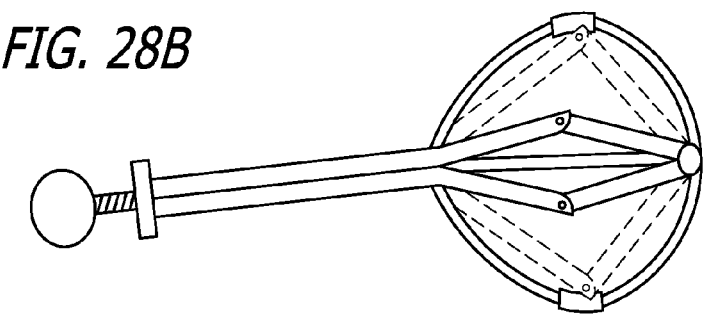
FIG. 28B shows the apparatus in a collapsed state.
Figure 28C:
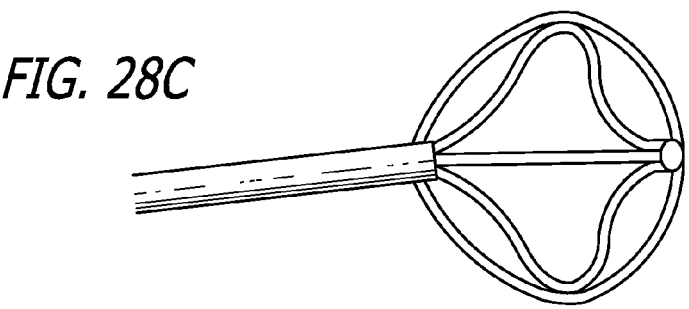
FIG. 28C shows yet another position for the apparatus inside a cavity.

Referring now to FIG. 28A, illustrated is yet another embodiment of a brachytherapy apparatus that includes supports for the tubes. As illustrated, a cable may be pulled to expand the tubes 2830 disposed inside a cavity. FIG. 28B shows the apparatus 2800 in a collapsed state. FIG. 28C shows yet another position for the apparatus inside a cavity.

Figure 29A:
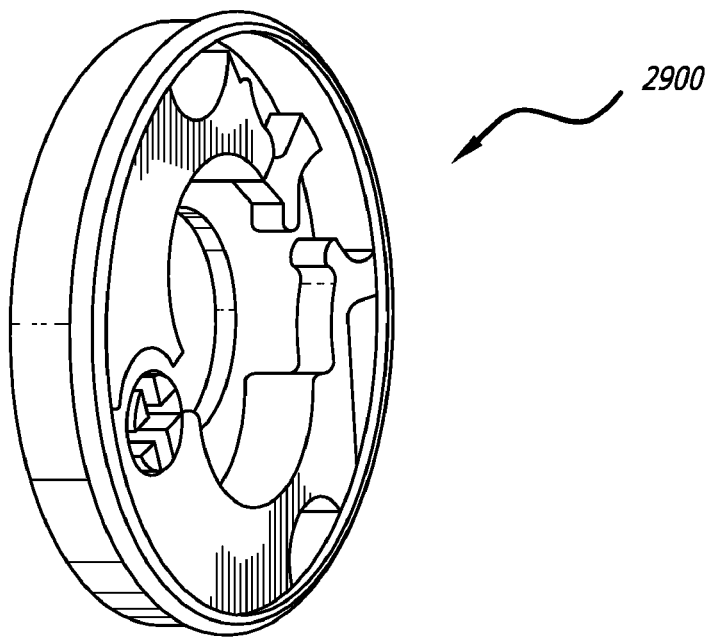
FIG. 29A is a perspective view of the cutting apparatus.
Figure 29B:
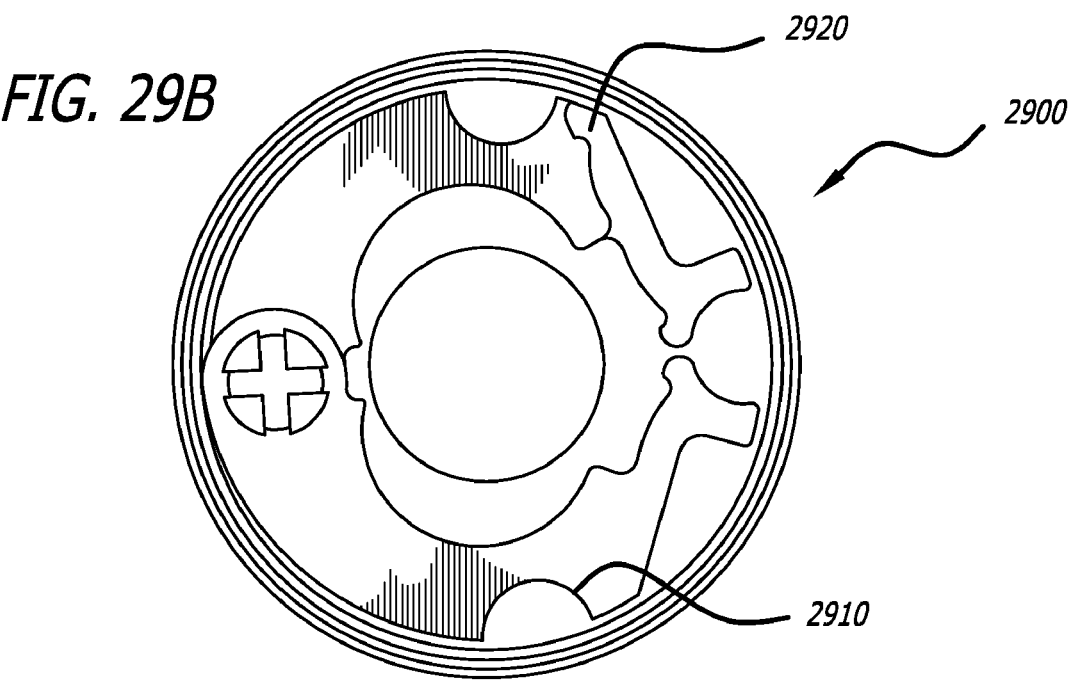
FIG. 29B a front view of the cutting apparatus with the scissor members in an open configuration.
Figure 29C:
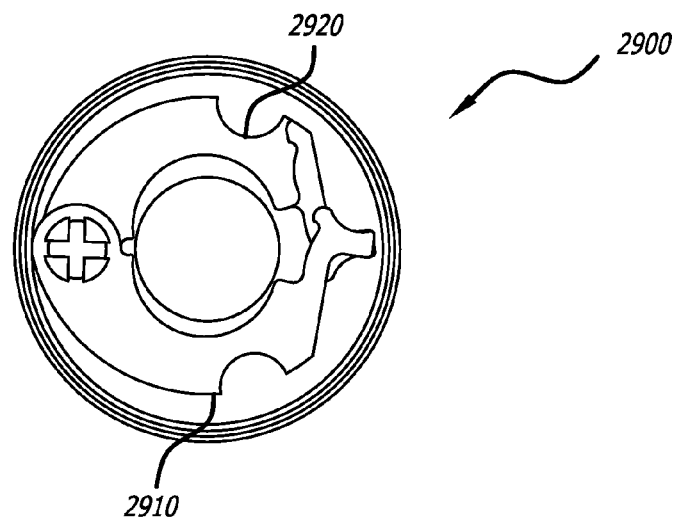
FIG. 29C shows the scissor members released.
Figure 29D:
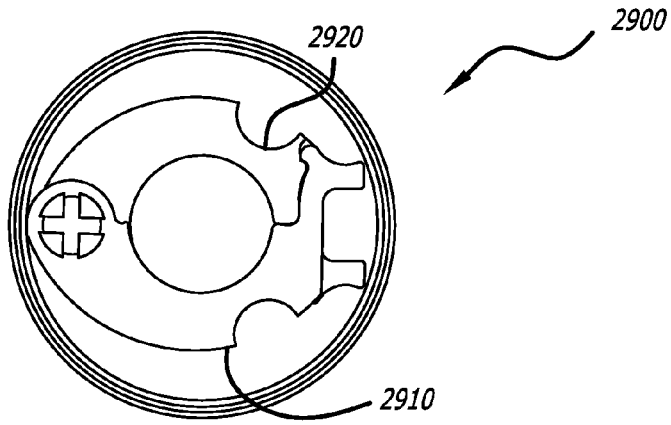
FIG. 29D shows the scissor members in a locked state.

FIGS. 29A-29D illustrate a scissor-type clamp apparatus for the thin-walled tubes. FIG. 29A is a perspective view of the apparatus 2900. FIG. 29B is a front view of the apparatus 2900 with the scissor members 2910, 2920 in an open configuration. FIG. 29C shows the scissor members 2910, 2920 released. FIG. 29D shows the scissor members 2910, 2920 in a locked state.

Figure 30:
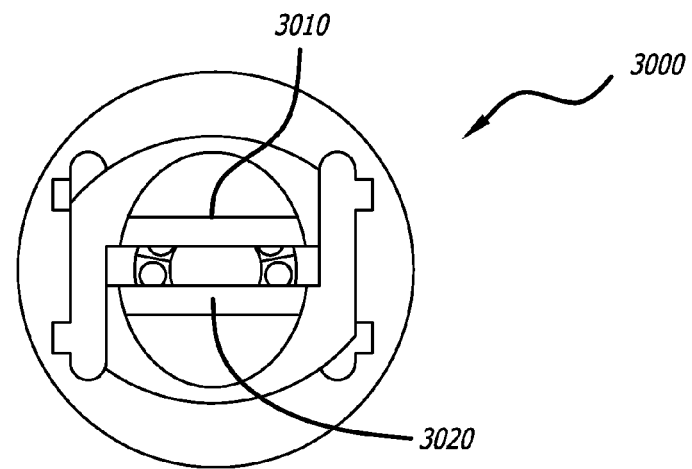
FIG. 30 is another clamp with cutter in accordance with one embodiment of the present disclosure.

Referring now to FIG. 30, illustrated is yet another clamp with cutter in accordance with one embodiment of the present disclosure. As illustrated, the clamp member 3000 includes blades 3010, 3020 that may be used to cut the thin-walled tubes.

Figure 31:
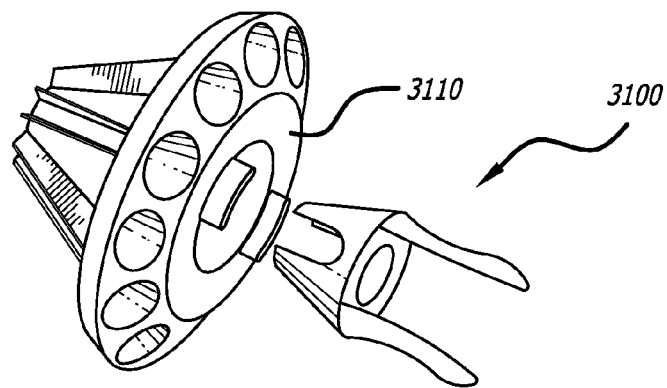
FIG. 31 is a cone clamp in accordance with one embodiment of the present disclosure.

Referring now to FIG. 31, illustrated is a cone clamp 3100 designed for use in a brachytherapy apparatus in accordance with one embodiment of the present disclosure. As illustrated, the cone clamp 3100 is designed to be squeezed and inserted into a conical member 3110, thus holding a center tube into place. If the center tube is pulled in a distal direction, the clamp 3100 would be more tightly squeezed. In order to release the clamp 3100, the clamp 3100 would be squeezed again.

Figure 32B:
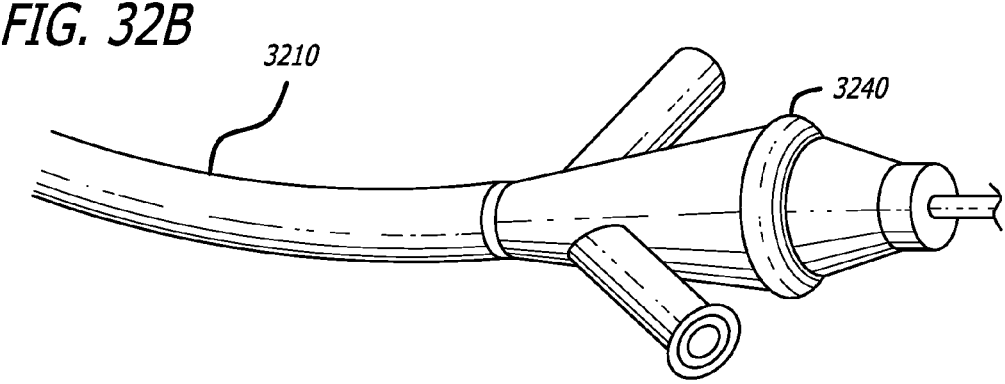
FIGS. 32A-32G illustrate an embodiment of a brachytherapy apparatus having a twist dial expansion apparatus and a gauge to meter the volume of expansion.
Figure 32C:
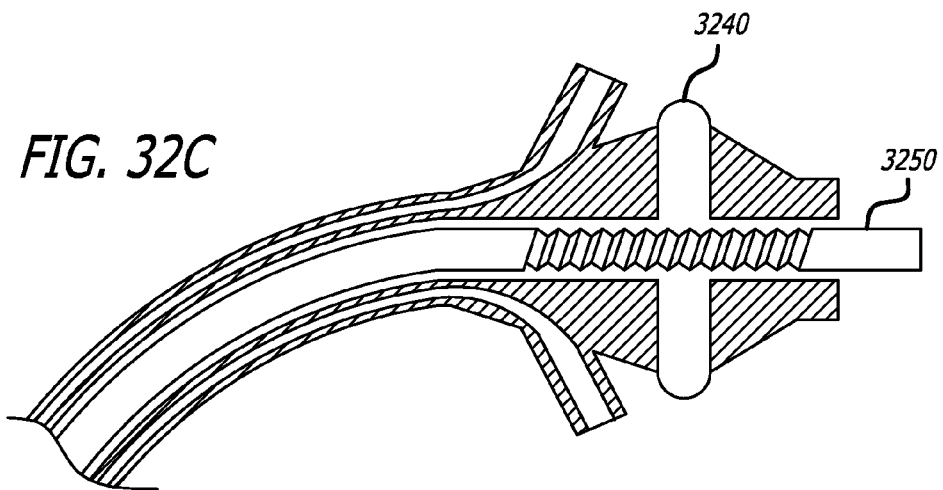
Figure 32A:
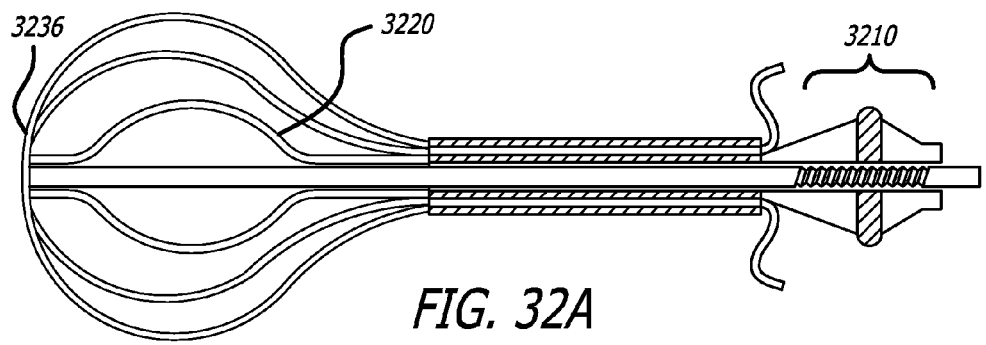

Referring now to FIG. 32A, illustrated is an embodiment of a brachytherapy apparatus 3200 having a twist dial expansion apparatus 3210. When the twist dial apparatus 3210 is turned clockwise, a wire or strip 3220 expands the plurality of tubes 3230 of the apparatus 3200. When the twist dial apparatus is turned in a counterclockwise direction, a wire or strip 3220 may collapse so that the plurality of tubes 3230 also collapse.

Referring now to FIG. 32B, illustrated is another view of the twist dial expansion apparatus 3210. Dial 3240 may be used to expand the apparatus.

Referring now to FIG. 32C, illustrated is a cross-sectional view of the twist dial expansion apparatus 3210. As shown, a threaded flexible screw 3250 may advance when the twist dial expansion apparatus 3240 is turned to expand the apparatus.

Figure 32F:
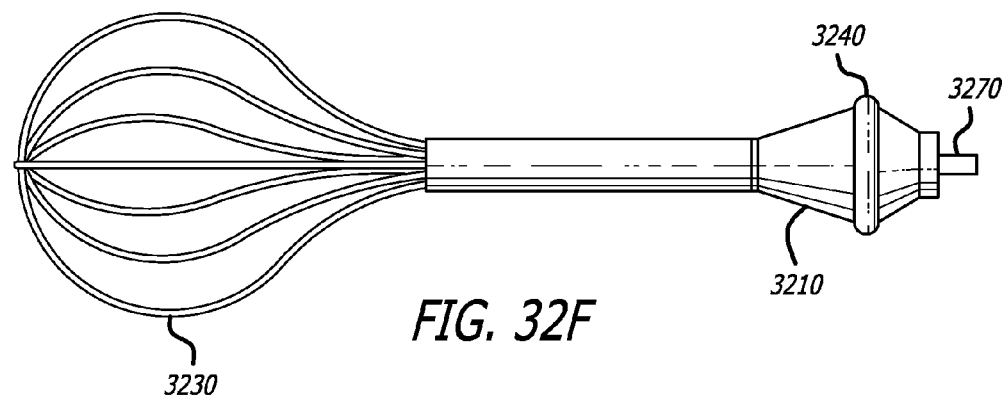
Figure 32G:
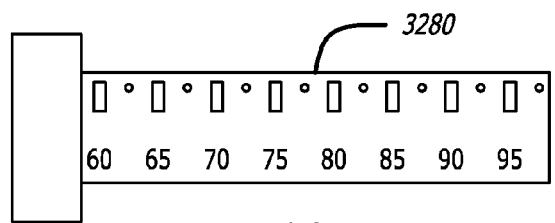
Figure 32D:
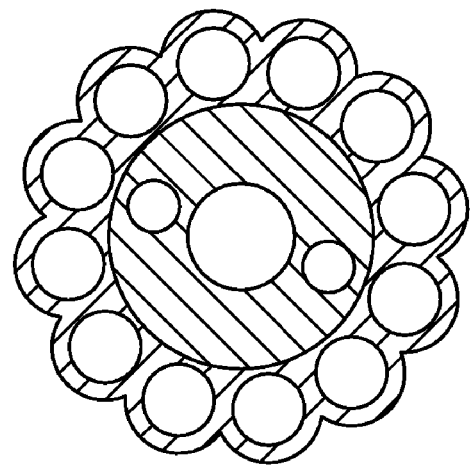

Referring now to FIG. 32D, illustrated is a single twist dial expansion apparatus having multiple tube openings.

Figure 32E:
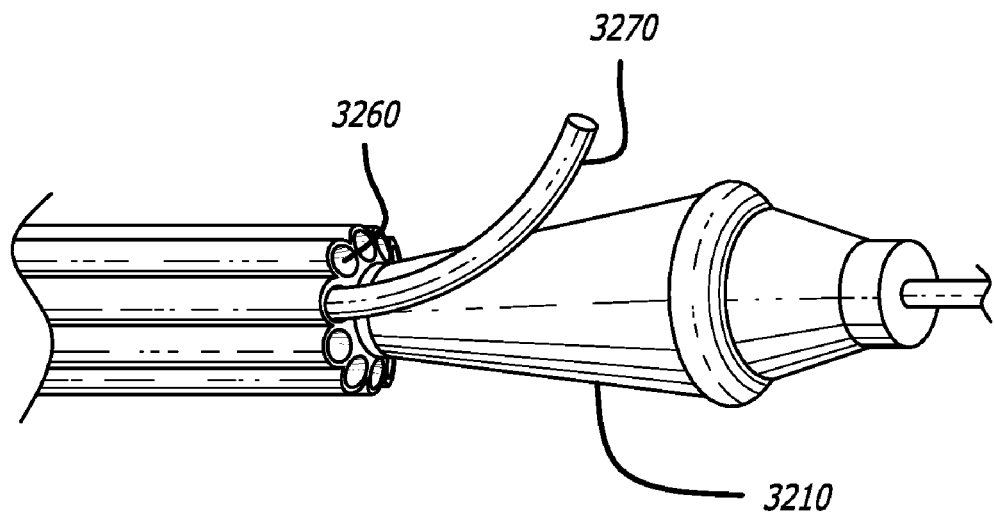

Referring now to FIG. 32E, illustrated is a view of the brachytherapy apparatus with openings 3260 and a seed strand 3270 being disposed therethrough.

Referring now to FIG. 32F, illustrated is the brachytherapy apparatus with a gauge 3270 to meter the volume of expansion. When the twist dial expansion apparatus 3240 is turned, the gauge 3270 may show the volume of expansion.

Referring now to FIG. 32G, illustrates is a gauge 3280 that may be used in conjunction with a brachytherapy apparatus. The gauge shows the volume of expansion in terms of cubic centimeters.

The brachytherapy apparatus of the present disclosure may take several forms. For example, the brachytherapy apparatus may be adjustable by a physician or other health care practitioner so that it accommodates the size of an asymmetrical body cavity. For the brachytherapy apparatus of the present disclosure, post-lumpectomy patients may be selected based on the size and shape of their surgical cavity.

The brachytherapy apparatus may be implanted into the patient prior to implanting the radioactive or therapeutic elements, e.g., radioactive seeds. In order to begin the implantation process for the brachytherapy apparatus, the physician may administer a local anesthetic to the patient.

Figure 33A:
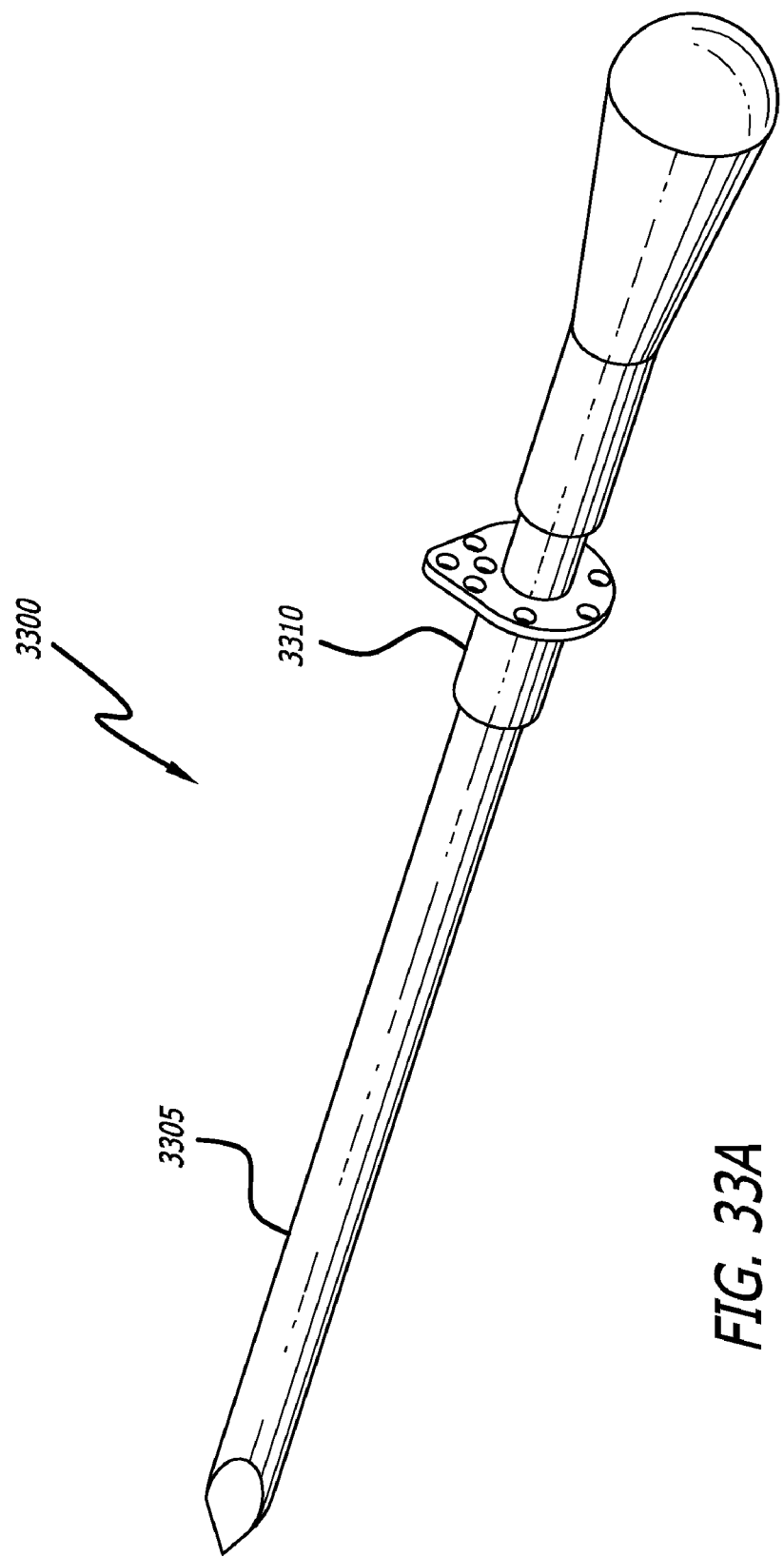
FIG. 33A is an introducer apparatus and other components that may be used to gain access to the post-lumpectomy cavity.

The entry site into the patient may be chosen based on access convenience and cavity geometry. Entry to the cavity may be gained in a number of ways. Referring now to FIG. 33A, illustrated is an introducer apparatus 3300 and other components that may be used to gain access to the post-lumpectomy cavity. A trocar 3305 which may be, e.g., a 9 millimeter trocar, may be inserted into a cavity. Sleeve 3310 may be left in the patient when the trocar 3305 is withdrawn from the patient, thus creating a conduit to the cavity.

Figure 33B:
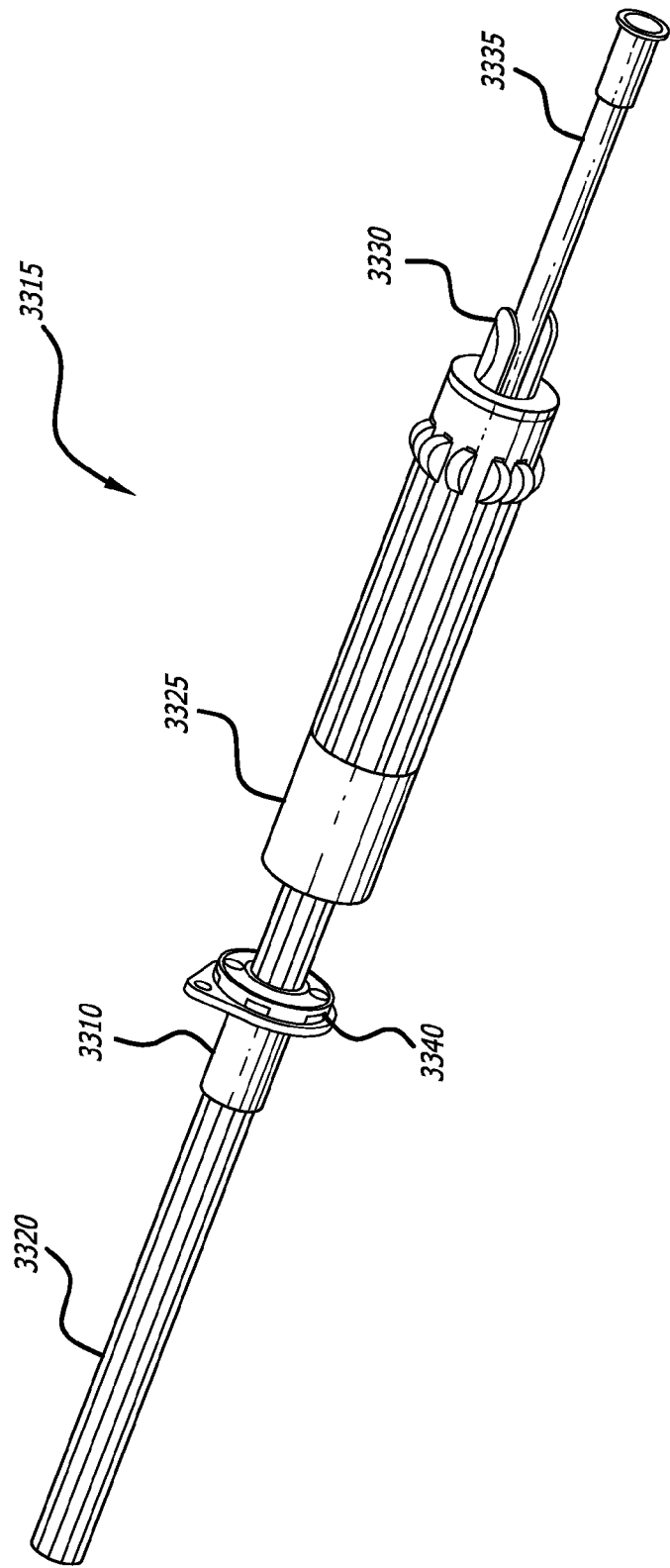
FIG. 33B shows a brachytherapy apparatus, including the sleeve of FIG. 33A that was left in the patient, as well as a plurality of thin-walled tubes.

Referring now to FIG. 33B, illustrated is a brachytherapy apparatus 3315, including the sleeve 3310 that was left in the patient and a plurality of thin-walled tubes 3320. Brachytherapy apparatus 3315 includes a whisk or tube adjuster 3325, a center core clamp 3330 and a center core 3335. Tube adjuster 3325 may be used to adjust the length of each of the plurality of thin-walled tubes 3320 as will be described in greater detail hereinbelow. Center core clamp 3330 may be used to clamp center core 3335. Center core 3335 may be used to support the various thin-walled tubes 3320 and may extend from the distal end near the thin-walled tubes 3320 to the proximal end.

A cutter (not shown) may also be provided to cut sleeve 3310 to a length that matches the skin to a cavity distance. The sleeve 3310 may then be sutured to the patient via suture disk 3375.

The brachytherapy apparatus or applicator 3315 may be introduced into the patient through the sleeve 3310 until the distal tip of the apparatus 3315 reaches the far end of the cavity. Using an imaging device, e.g., computerized tomography (CT) or an ultrasound which are known in the art, the physician may expand the distal portion of the applicator 3315 into a symmetrical "whisk" with twelve (12) tubes. It should be understood that the number of tubes may vary depending upon a particular design and patient's needs.

The physician may expand the tubes 3320 when he/she pulls the center core 3335 in order to extend outwardly the plurality of thin-walled tubs 3320 into a substantially circular configuration around the center core 3335 at the distal end. The thin-walled tubes 3320 may be configured in two substantially concentric circles. If greater length is needed for the thin-walled tubes 3320 in order to accommodate a larger cavity, the sleeve 3310 may be pulled in a proximal direction in order to create a longer set of tubes. If desired, the physician again may pull the center core 3335 in a proximal direction to increase the diameter of the two substantially concentric circles.

Figure 33C:
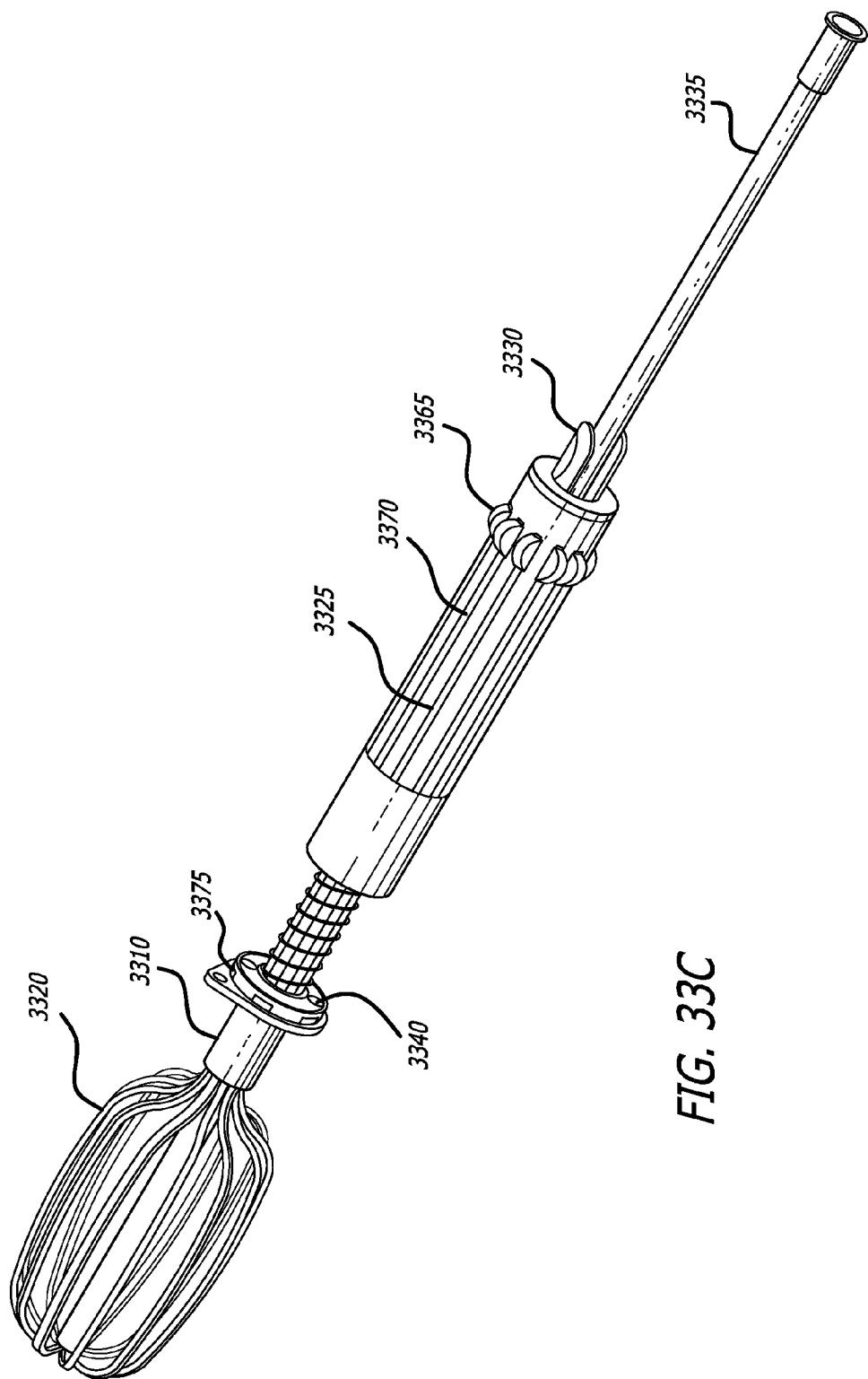
FIG. 33C is a brachytherapy apparatus in accordance with another embodiment of the present disclosure.

Referring now to FIG. 33C, illustrated is the brachytherapy apparatus of FIG. 33B in its expanded state. For patients with asymmetrical cavities, the lengths of the individual tubes also may be adjusted to accommodate the size and/or shape of the cavity. This adjustment action may be accomplished when the physician pushes one of the raised projections, e.g., 3365 along and within one of the guides, e.g., 3370 to advance the individual tube, thus lengthening the tube to accommodate the cavity's larger sections. Each individual tube may have a corresponding raised projection as well as a guide.

After confirming the placement of the plurality of thin-walled tubes 3320, the physician may lock the tubes 3320 to the sleeve 3310. The physician may have determined that the tubes were sufficiently expanded outwardly based on the pressure and/or resistance he or she feels when the brachytherapy apparatus touches the wall of the cavity. It should be noted that sleeve 3310 also has a suture disk 3375 near its proximal end. The suture disk 3375 may be used later to suture the thin-walled tubes 3320 of the brachytherapy apparatus inside a patient. At this point, the physician has locked the tubes 3320 to the sleeve 3310 by the tube clip or "whisk clip" 3340.

The physician may use a cutter to remove the portion of the apparatus that is outside of the patient. Referring now to FIG. 33D, illustrated is the brachytherapy apparatus of FIG. 33C with a cutter 3345 that may be used for these purposes.

Figure 33E:
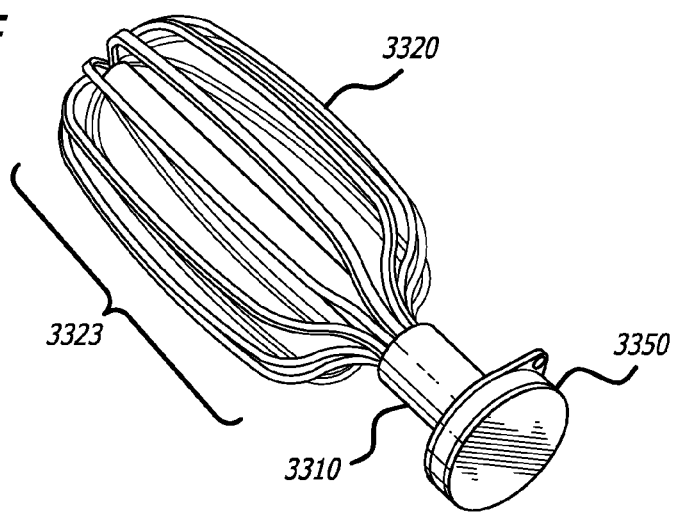
FIG. 33E is the brachytherapy apparatus or catheter of FIG. 33D with a cap placed on its proximal end.

Referring now to FIG. 33E, illustrated is the portion of the brachytherapy apparatus of FIG. 33D that remains after the tubes have been cut. This portion of the apparatus may be referred to as the brachytherapy catheter 3323 and may include the thin-walled tubes 3320 and the center core 3335 that remains after the tubes have been cut. As shown, the catheter 3323 has appended thereto a cap 3350 at its proximal end. The cap 3350 may be affixed onto the catheter 3323 when the patient is sent home. The catheter 3323 may remain in the cavity, along with its accompanying components until the patient returns for further treatment or the brachytherapy catheter 3323 and accompanying components are removed.

The patient may be sent home with wound care instructions. The patient may return to have the radioactive seeds or sources implanted at a later date. Before the patient returns, a physician or other health care professional may develop a treatment plan based on the image of the expanded brachytherapy apparatus that includes the plurality of thin-walled tubes 3320. One or more tubes 3320 may be radiopaque and have a different color from the others for purposes of identification during the imaging process.

The radioactive sources may arrive pre-stranded in a radiation-shielded seed transporter. Referring now to FIG. 33F, illustrated is a brachytherapy catheter 3323 with a seed transporter 3355 in accordance with one embodiment of the present disclosure. The seed transporter 3355 may have a substantially cylindrical body with an opening 3390 along a side. The physician may engage the seed transporter 3355 to the brachytherapy catheter 3323 that has been deployed and cut. At the proximal end of seed transport 3355 may be openings 3395 that correspond to each of the thin-walled tubes 3320 of the brachytherapy catheter 3323. The physician may then push radioactive stranded seeds into the apparatus 3315 using an obturator (not shown) and an adapter (not shown). The adapter will be described in greater detail hereinbelow.

After the implanted radioactive seeds have been imaged and compared to the treatment plan, the excess strands—representing the tail end of the thin-walled tubes 3320—outside the apparatus 3320 may be trimmed to a short length, e.g., ⅛ of an inch, which may allow the physician to remove the strands at a later time. The apparatus 3315 may be recapped, and the patient may be discharged with a radiation shielding bra. Such bras are known in the art.

The design of the brachytherapy apparatus of the present disclosure may permit the physician to remove some stranded seeds in the middle of the treatment period if desired. For example, there may be a need for reducing the dosage of radiation to certain areas of the cavity, e.g., areas close to the skin or near the chest wall. According to the treatment plan, the patient may return several days later to have the apparatus 3315 and corresponding seeds removed.

The cap may be removed by the physician, and the stranded seeds may be removed from the apparatus 3315 by a pair of tweezers (not shown). The tweezers may be operated from within a shielded container. The physician may employ a whisk removal tool in order to remove the apparatus 3315 from the patient.

Figure 33G:
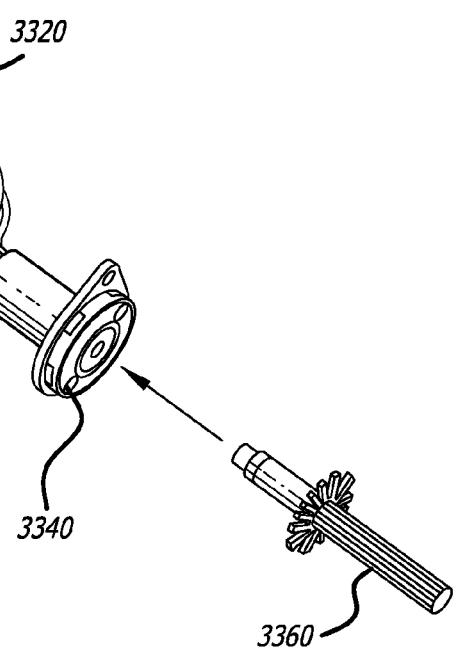
FIG. 33G is a brachytherapy catheter and a whisk removal tool in accordance with one embodiment of the present disclosure.
Figure 33F:
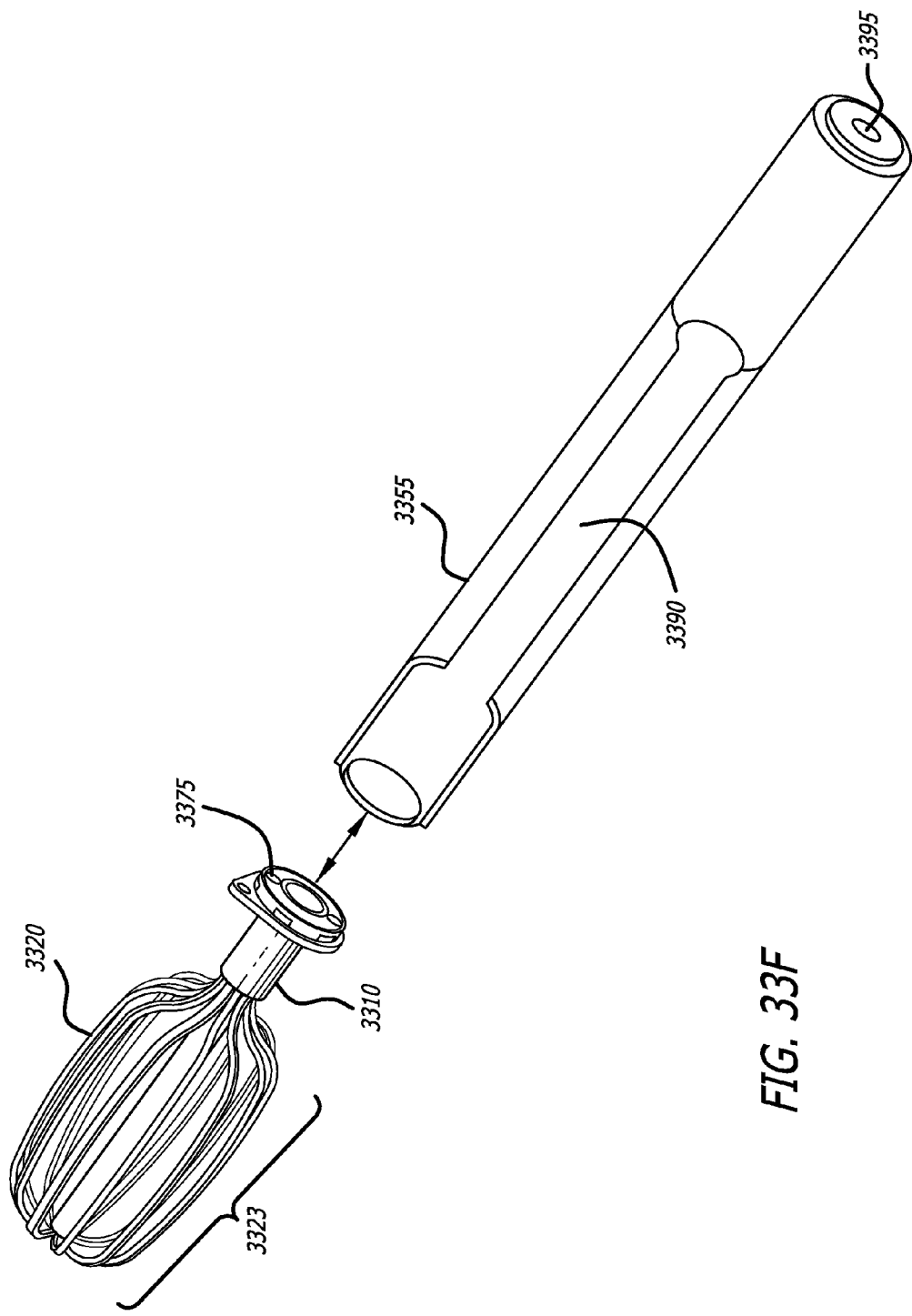
FIG. 33F is a brachytherapy apparatus with a seed transporter in accordance with one embodiment of the present disclosure.

Referring now to FIG. 33G, illustrated is a brachytherapy catheter and a whisk removal tool in accordance with one embodiment of the present disclosure. After loosening the whisk clip 3340, the physician may collapse the whisk by straightening individual thin-walled tubes 3320 and attach each of the individual thin-walled tubes to the whisk removal tool 3360. The physician may then remove the apparatus from the patient.

Figure 34:
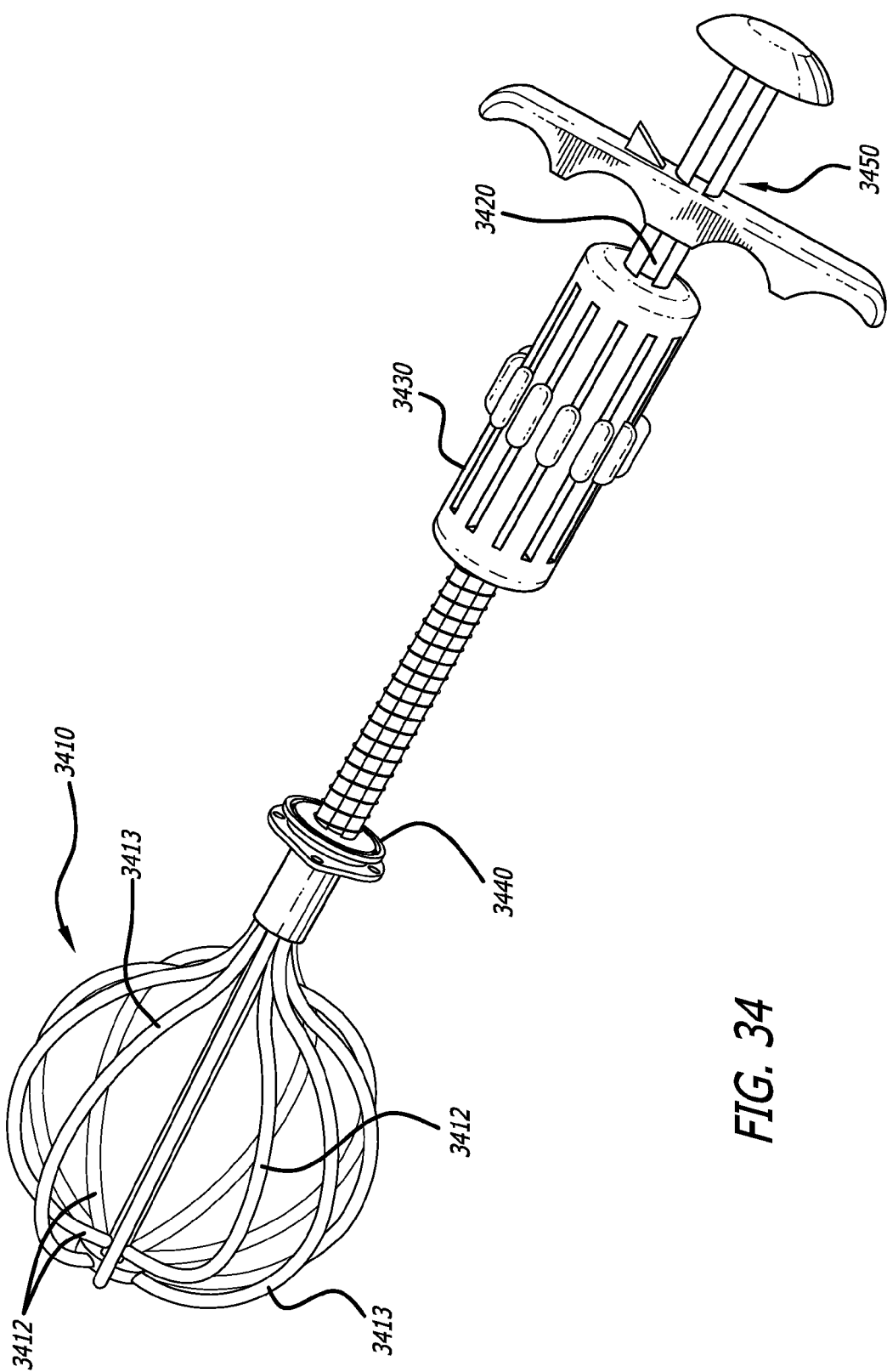
FIG. 34 is a brachytherapy apparatus having a conformable applicator and tubes configured in two substantially concentric circles in accordance with another embodiment of the present disclosure.

Referring now to FIG. 34, illustrated is a brachytherapy apparatus having a conformable applicator and tubes configured in two substantially concentric circles in accordance with yet another embodiment of the present disclosure. This brachytherapy apparatus 3400 may be used with both high-dose and low-dose radiation treatments.

The conformable applicator or apparatus includes whisk tubing 3410, a center core 3420, a whisk expander 3450, a whisk adjuster 3430, and whisk clips 3440.

The number of thin-walled tubes 3410 in this embodiment is twelve (12). However, as previously noted, the number of tubes may vary according to the needs and desires of the physician and patient.

The thin-walled tubes 3410 may be arranged into two concentric circles around the center core 3420. For example, tube 3412 is interior to tube 3413. The distal ends of the thin-walled tubes 3410 and the center core 3420 may be joined together, thus allowing the conformable apparatus 3400 to be inserted through a small sleeve, e.g., a 9 mm sleeve in diameter, into a body cavity.

The whisk expander 3450 may be used to overcome the initial resistance to expansion by the plurality of thin-walled tubes 3410. Once activated, the whisk expander 3450 may push the proximal ends of the plurality of thin-walled tubes 3410 in a distal direction, thereby forcing the thin-walled tubes 3410 to expand into the double-layered whisk as shown.

The whisk adjuster 3430 may permit the physician to change the shape of the thin-walled tubes 3410 by moving individual tubes in a distal direction or, alternatively, in a proximal direction, which may allow the thin-walled tubes 3410 to conform to shape of a body cavity.

After the whisk adjustment is completed, the whisk clips 3440 may be used to lock the thin-walled tubes 3410 and the center core 3420 together in order to resist changing the shape of the thin-walled tubes 3410.

The proximal portion of the conformable apparatus 3400 that is at or just proximal to the whisk clips 3440 may be cut off, thus exposing the lumens of the thin-walled tubes 3410 as well as the center core 3420. One or more radiation sources may then be inserted into the thin-walled tubes 3410.

For high dose rate (HDR) radiation treatment, the radiation source may be placed in the center core lumen and, if desired, the lumens of the inner layer in the double whisk. After each treatment, the radiation source may be removed from the patient, but the conformable apparatus 3400 may remain in patient until all treatments are completed.

For low dose rate (LDR) radiation treatment, stranded radiation sources may be inserted into the lumens of the double-layered thin-walled tubes 3410 that form two substantially concentric circles. These radiation sources may remain in the patient for the duration of treatment. The patient may wear a radiation shield to prevent unwanted radiation to other people as well as other undesirable radiation exposure.

At the end of the treatment, the radiation sources may be removed. A whisk removal tool may be attached to the conformable applicator 3400, and the whisk clips 3440 may be disengaged. After all the plurality of thin-walled tubes 3410 is straightened by the whisk removal tool, the conformable apparatus 3400 may be pulled out of the patient.

Figure 35A:
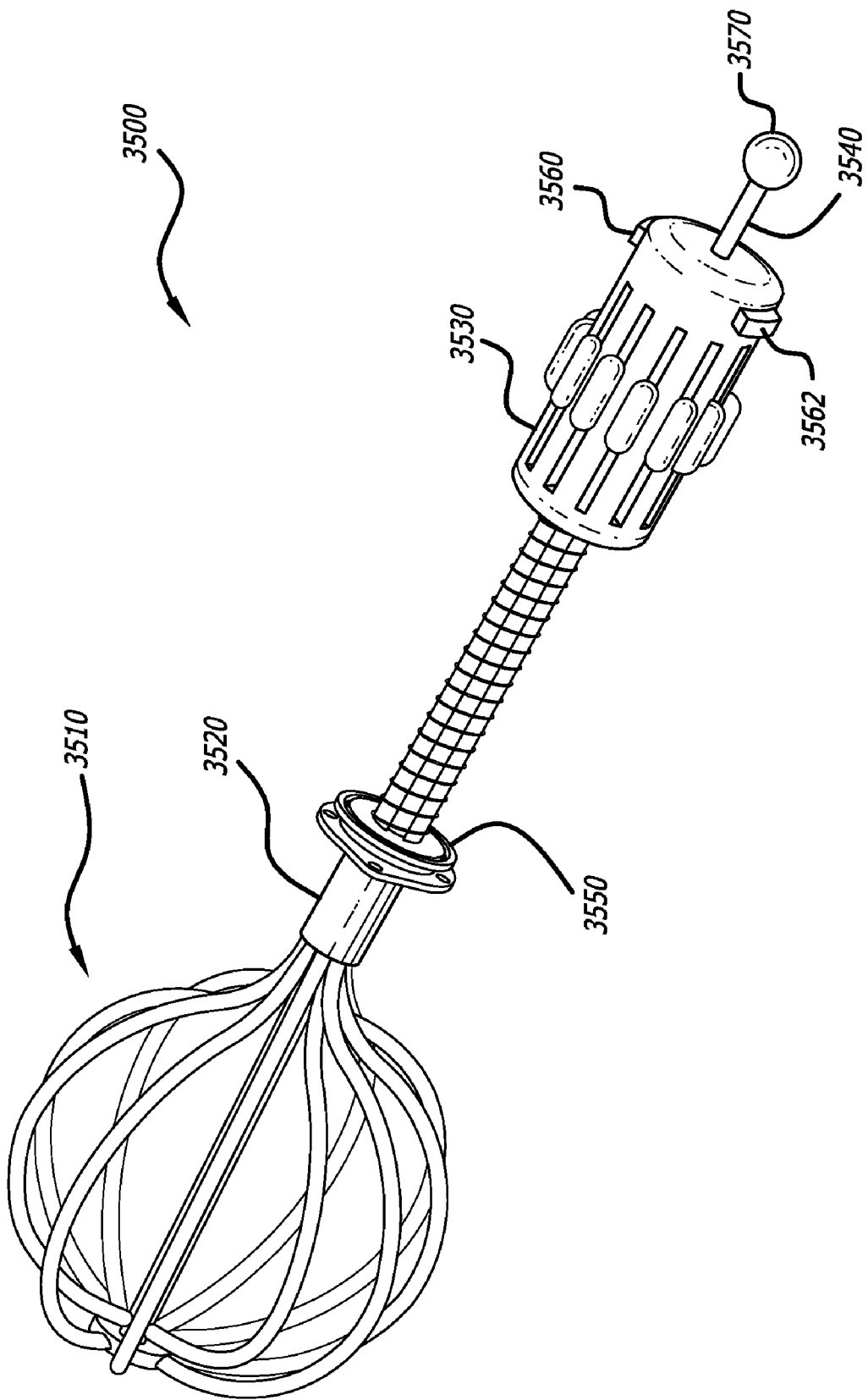
FIGS. 35A and 35B show a brachytherapy apparatus having tubes that form two substantially concentric circles in accordance with yet another embodiment of the present disclosure.

Referring now to FIG. 35A, illustrated is another embodiment of a brachytherapy apparatus having tubes that form two substantially concentric circles. In this embodiment, the brachytherapy apparatus 3500 includes a plurality of thin-walled tubes 3510, a center core 3540, a whisk adjuster 3530, and whisk clips 3550.

In accordance with this embodiment and as in the earlier embodiment, the plurality of thin-walled tubes 3510 numbers twelve (12). In the expanded position as shown, the thin-walled tubes 3510 may be arranged in two concentric circles around the center core 3540. The distal ends of the plurality of thin-walled tubes 3510 and the center core 3540 may be joined, thus allowing the thin-walled tubes 3510 to be inserted through a sleeve 3520 into a body cavity. The sleeve 3520 may be small in diameter, e.g., 9-mm in diameter. The center core 3540 may serve as a whisk expander 3560 and may be used to overcome the straight whisk tubing's initial resistance to expansion.

Figure 35B:
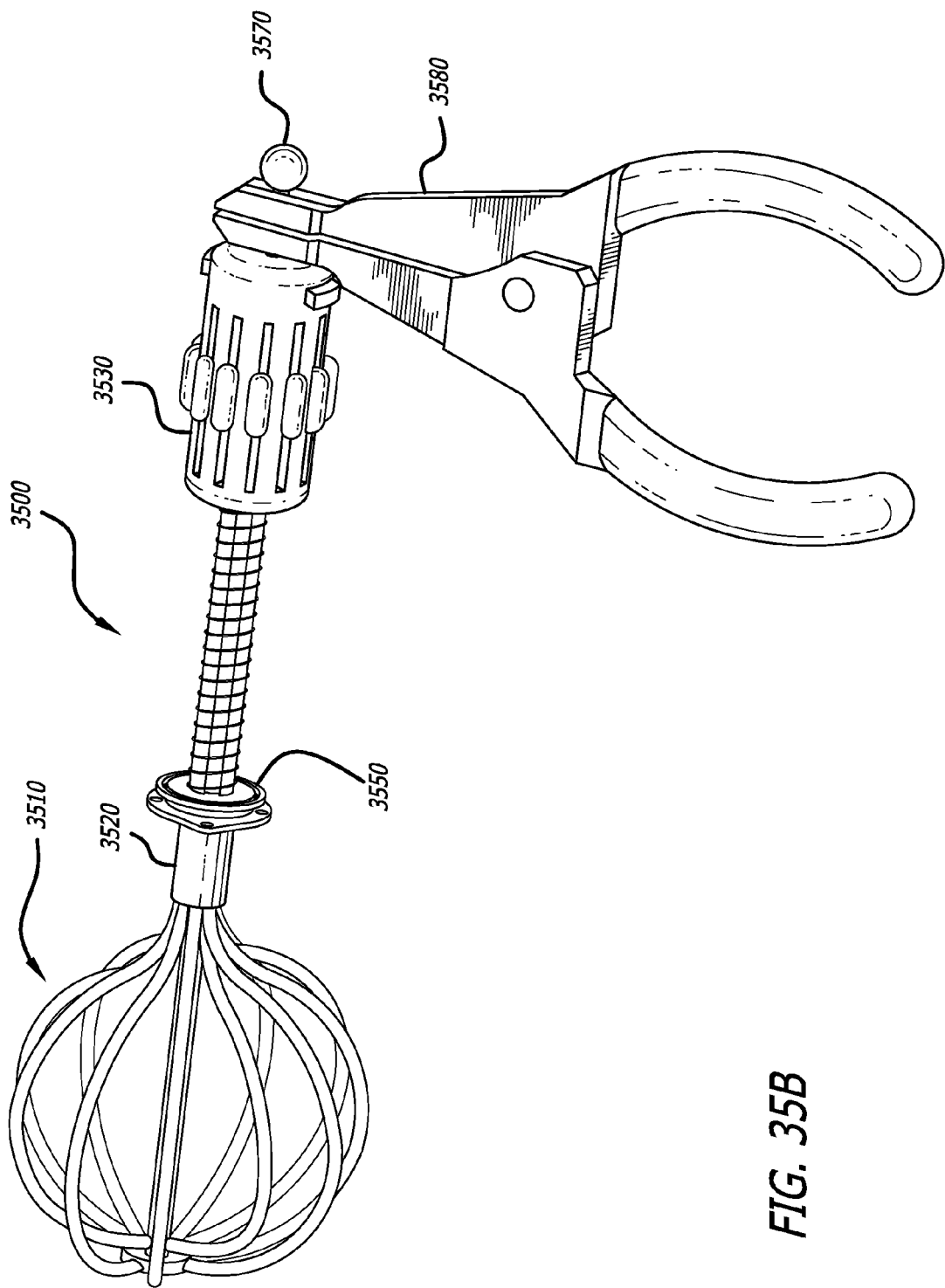

Referring now to FIG. 35B, illustrated is an example of how the whisk may be expanded. The physician may place a whisk expansion tool 3580 on the center core 3540 that extends substantially from the proximal end to the distal end of the apparatus 3500. By gripping the center core 3540 with the whisk expansion tool 3580 at the portion just between the whisk adjuster 3530 and the center core end cap 3570, the physician may pull the center 3540 in a proximal direction, and thereby push the thin-walled tubes 3510 in a distal direction. In this manner, the thin-walled tubes 3510 are forced to expand outwardly into the double layered whisk as shown.

The apparatus 3500 may include a one-way mechanism that assists in preventing the center core 3540 from traveling back in a distal direction when the whisk expansion tool 3580 is removed. Release mechanisms 3560, 3562 may also be included for the one-way mechanism so the center core 3540 can be adjusted back in a distal direction. These release mechanisms 3560, 3562 may be a set of diametrically opposed buttons configured to be pressed in order to release of the center core 3540 so that the center core 3540 may travel in a distal direction.

Figure 35C:
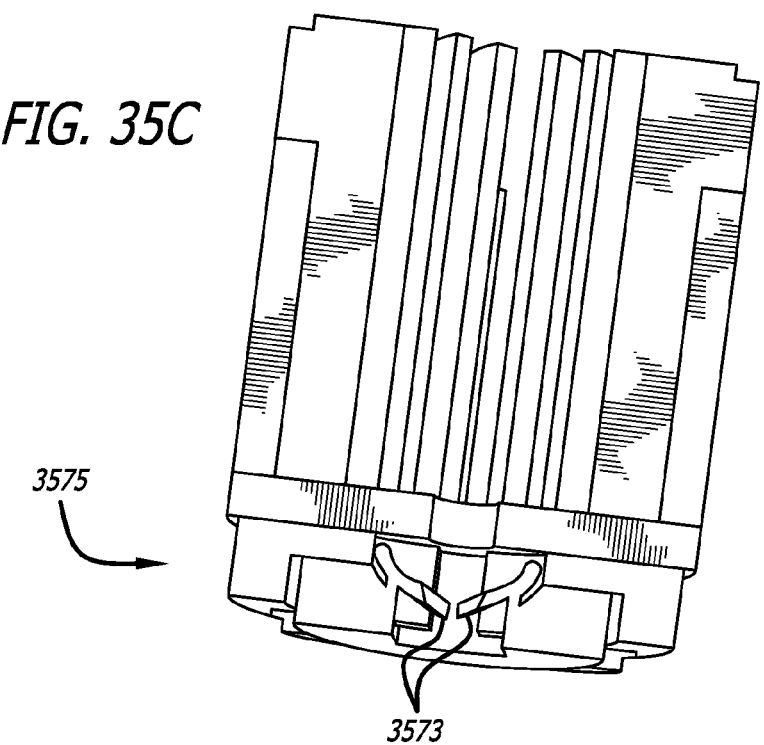
FIGS. 35C and 35D show a one-way mechanism that prevents the center core from moving in a first direction, and its counterpart release mechanism that permits movements of the center core in a second direction.
Figure 35D:
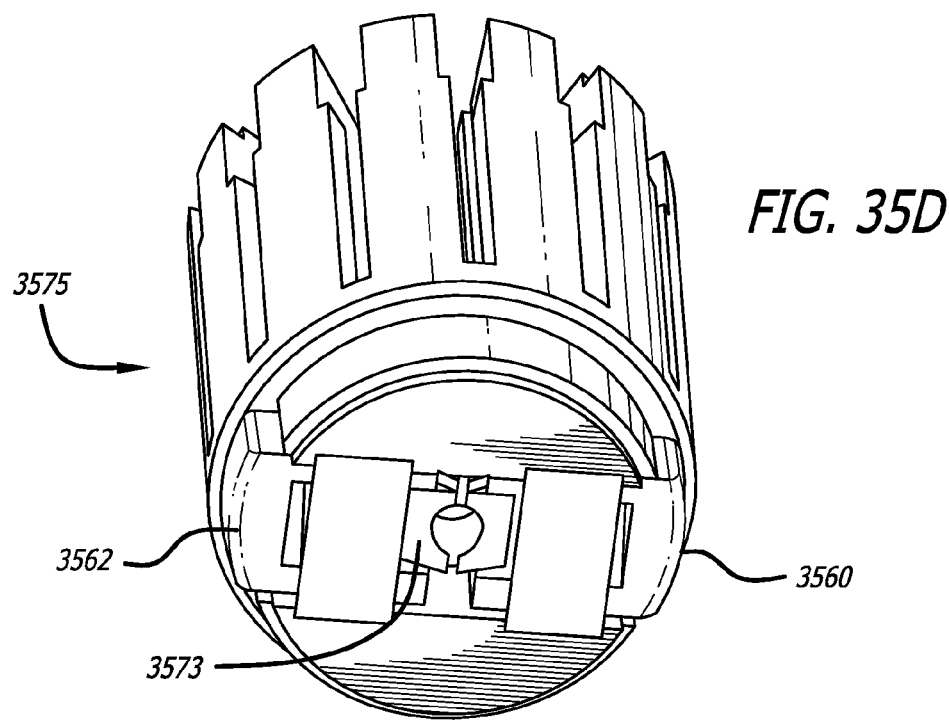

Referring now to FIG. 35C, illustrated is side view of a one-way mechanism 3575 that assists in preventing the center core from traveling back when the whisk expansion tool is removed. As shown, the one-way mechanism includes jaws 3573 that prevent the center core from traveling back when the whisk expansion tool is removed. Referring now to FIG. 35D, illustrated is another view of the one-way mechanism 3575 of FIG. 35C. When the release mechanisms 3560, 3562 are engaged, the jaws 3573 retract, thus allowing the center core to move in a proximal direction.

Now referring back to FIG. 35B, the whisk adjuster 3530 may permit the physician to change the shape of the expanded plurality of thin-walled tubes 3510 by moving individual tubes in a distal direction or a proximal direction or a distal direction, thus allowing the expanded tubes 3510 to conform to shape of the body cavity into which they have been inserted or implanted.

Once the physician has completed the whisk adjustment, the whisk clips 3550 may be used to lock the tubes 3510 and the center core 3540 together in place so that the shape of the tubes that have been expanded outwardly does not change.

The portion of the brachytherapy apparatus that is proximal to the whisk clips 3550 may then be cut off, thus exposing the lumens of the tubes 3510 and center core 3540 for insertion of the radiation source or sources.

If high dose rate (HDR) radiation treatment is planned, the radiation source may be inserted into the lumen of the center core 3540 after the tubes 3510 have been inserted or implanted into the cavity. Moreover, if desired, one or more radiation sources may be inserted or implanted into the lumens of one or more of the tubes 3510 either in lieu of or in addition to the lumen of the center core 3540.

Figure 36:
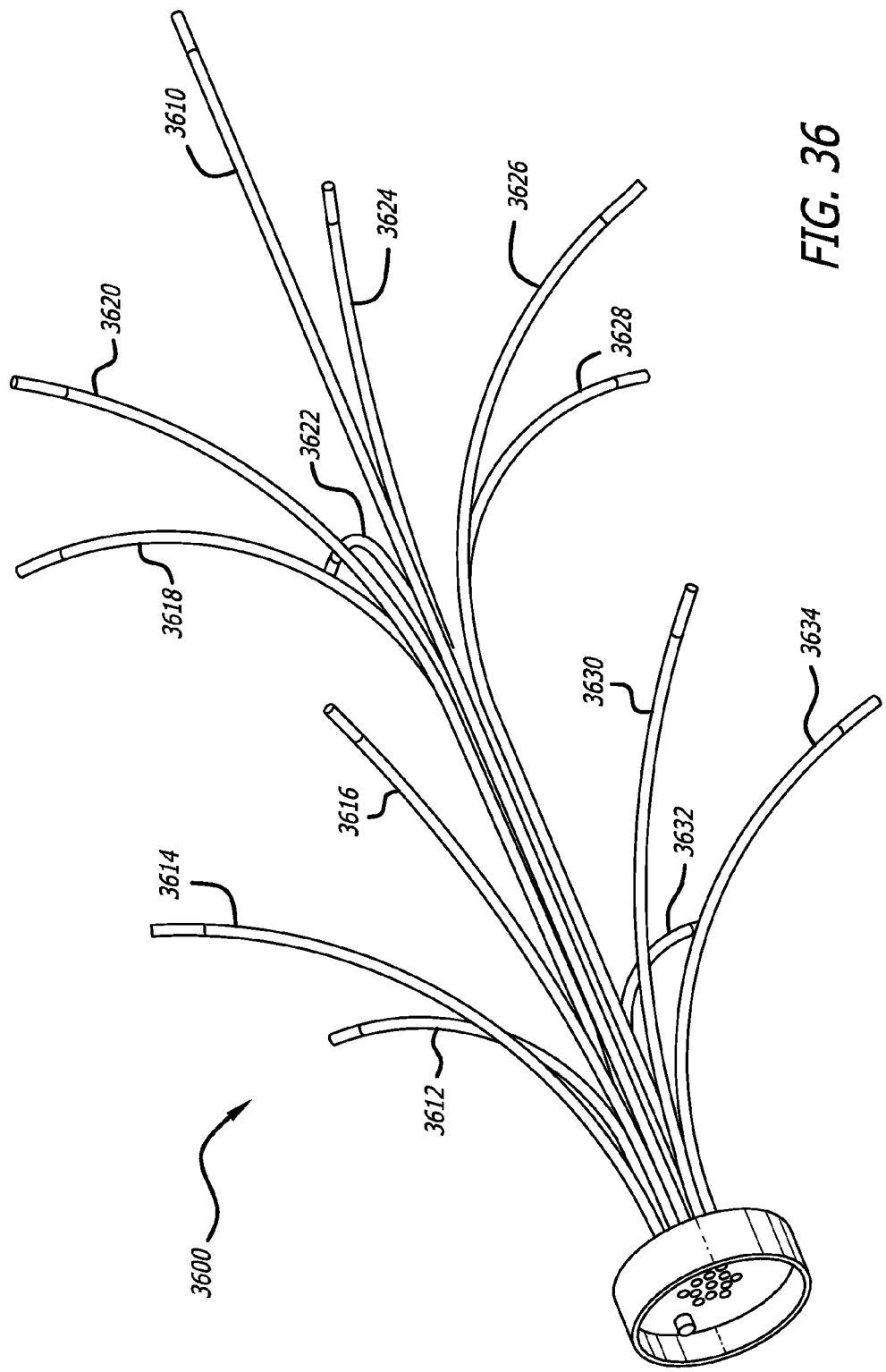
FIG. 36 is an adaptor device designed to facilitate insertion of radiation sources into the lumen of the center core and/or the tubes of FIGS. 35A and 35B.

Referring now to FIG. 36, illustrated is an adaptor device designed to facilitate insertion of radiation sources into the lumen of the center core and/or the tubes of FIG. 35A. This HDR adapter is designed to facilitate the connection of HDR afterloader machines to the thin-walled tubes and/or center core. The HDR afterloader may include a computer that controls and implements insertion of a radiation source into the center core and/or thin-walled tubes of the brachytherapy apparatus. Such afterloader machines are commercially available as VARIAN™, GAMMAMED™ or NUCLETRON™ afterloader machines. The computer may then control how long the radiation source dwells in different portions of the cavity based on the isodose profile.

This removable high-dose rate (HDR) adaptor 3600 may be mounted to the brachytherapy apparatus. The HDR adapter may include thirteen flexible tubes, with the center tube 3610 being configured to connect an afterloader device to the brachytherapy apparatus. The remaining twelve HDR adapter tubes 3612, 3614, 3616, 3618, 3620, 3622, 3624, 3626, 3628, 3630, 3632 and 3634 correlate to the twelve (12) tubes of the brachytherapy apparatus.

After each treatment, the radiation source and the HDR adaptor 3600 may removed from the brachytherapy apparatus, but the tubes of brachytherapy apparatus itself may remain in the patient until all treatments are completed.

The brachytherapy apparatus and accompanying adapter of FIGS. 35A and 36, respectively, may also be used in low dose rate (LDR) radiation treatment. More particularly, each desired stranded radiation source may be inserted into the thin-walled tubes and/or center core lumens individually through an LDR adapter. Alternatively, the stranded radiation sources may be stranded together through a seed transport device, which may include both a shielded shipping container and the LDR adapter. The LDR adapter or the transfer device may be removed after the LDR radiation sources are inserted into the thin-walled tubes and/or center core lumen. Since the LDR radiation sources may remain in the patient for as long as it takes to deliver a prescribed dose of radiation, the patient may need to wear a radiation shield to prevent unwanted radiation exposure. At the end of the treatment, the radiation sources may be removed, regardless of whether HDR radiation sources or LDR radiation sources are used.

While the specification describes particular embodiments of the present invention, those of ordinary skill can devise variations of the present invention without departing from the inventive concept.

The invention claimed is:

1. A brachytherapy system for delivery of localized irradiation to tissue near a cavity that lies beneath a surface of a body comprising:
    a brachytherapy device that comprises a plurality of cavity tubes configured to be inserted within the cavity and to controllably move from a collapsed state to an expanded state while within the cavity, each cavity tube having a lumen configured to house at least one radioactive source, and a center core having a lumen for supporting the plurality of cavity tubes; and
    an adapter configured to be removably mounted to the brachytherapy device and to facilitate the connection of an afterloader machine to each of the cavity tubes and the center core so as to permit the afterloader machine to insert at least one radiation source into the lumens of each of the cavity tubes and the center core, and to permit the afterloader machine to control the movement of the at least one radiation source within the lumens of each of the cavity tubes and the center core, the adapter having a plurality of adapter tubes, each adapter tube being corresponding to one of the plurality of cavity tubes, and an opening at a distal end of each adapter tube.

2. The brachytherapy system of claim 1 wherein the adapter comprises an adapter tube corresponding to the center core and there is an opening at the distal end of the adapter tube.

3. The brachytherapy system of claim 2 further comprising a cap-like structure to which the end of the adapter tube corresponding to the center core is connected, the cap-like structure having an opening therein that corresponds to the lumen in the adapter tube corresponding to the center core.

4. The brachytherapy system of claim 1, wherein the plurality of adapter tubes are flexible.

5. The brachytherapy system of claim 1, further comprising a cap-like structure to which one end of each of the plurality of adapter tubes is connected, the cap-like structure having openings therein that correspond to each of the lumens in the plurality of adapter tubes.

* * * * *